US008492141B2

(12) United States Patent
Azar et al.

(10) Patent No.: US 8,492,141 B2

(45) Date of Patent: Jul. 23, 2013

(54) NEOSTATINS

(75) Inventors: Dimitri T. Azar, Chicago, IL (US); Jin-Hong Chang, Clarendon Hills, IL (US)

(73) Assignee: Massachusetts Eye & Ear Infirmary, Boston, MA (US)

( * ) Notice: Subject to any disclaimer, the term of this patent is extended or adjusted under 35 U.S.C. 154(b) by 0 days.

(21) Appl. No.: 12/766,741

(22) Filed: Apr. 23, 2010

(65) Prior Publication Data

US 2010/0331396 A1 Dec. 30, 2010

Related U.S. Application Data

(60) Continuation of application No. 11/965,411, filed on Dec. 27, 2007, now abandoned, which is a division of application No. 11/346,490, filed on Feb. 1, 2006, now Pat. No. 7,662,945.

(60) Provisional application No. 60/649,029, filed on Feb. 1, 2005.

(51) Int. Cl.

| | |
|---|---|
| ***C12N 15/00*** | (2006.01) |
| ***C12N 5/00*** | (2006.01) |
| ***C12N 5/02*** | (2006.01) |

(52) U.S. Cl.
USPC ......................... 435/320.1; 435/325; 435/455

(58) Field of Classification Search
USPC ....................... 435/320.1, 325, 455; 536/23.4
See application file for complete search history.

(56) References Cited

PUBLICATIONS

Chang et al., Curr Opin Ophthalmol. Aug. 2001;12(4):242-9. Corneal neovascularization. Abstract.*

Azar, Dimitri T.; Corneal Angiogenic Privilege: Angiogenic and Antiangiogenic Factors in Corneal Avascularity, Vasculogenesis, and Wound Healing (An American Ophthalmological Society Thesis); Trans Am. Ophthalmol. Soc.; 2006; pp. 104:264-302.

Chang et al; Functional characterization of neostatins, the MMP-derived, enzymatic cleavage products of type XVIII collagen; FEBS Letters; 2005; pp. 579:3601-3606.

Ellenberg et al; Novel aspects of corneal angiogenic and lymphangiogenic privilege; Progress in Retinal and Eye Research; 2010; pp. 29:208-248.

Kojima et al; Neostatin-7 regulates bFGF-induced corneal lymphangiogenesis; FEBS Letters; 2008; pp. 582:2515-2520.

Zhou et al; Impaired endochondral ossification and angiogenesis in mice deficient in membrane-type matrix metalloproteinase I; PNAS; 2000; pp. 97(8):4052-4057.

* cited by examiner

*Primary Examiner* — Maria Leavitt

(74) *Attorney, Agent, or Firm* — Fish & Richardson P.C.

(57) ABSTRACT

The invention provides fragments of type XVIII collagen termed neostatins, and methods for their use in the treatment of opthalmological disorders associated with angiogenesis.

13 Claims, 16 Drawing Sheets

Neostatin-7 human DNA/protein sequences

```
  1 CTGCACGACA GCAACCCCTA CCCGCGGCGG GAGCACCCCC ACCCCACCGC
    L  H  D  S   N  P  Y   P  R  R   E  H  P  H   P  T  A
 51 GCGGCCCTGG CGGGCAGATG ACATCCTGGC CAGCCCCCCT CGCCTGCCCG
     R  P  W   R  A  D  D   I  L  A   S  P  P   R  L  P  E
101 AGCCCCAGCC CTACCCCGGA GCCCCGCACC ACAGCTCCTA CGTGCACCTG
     P  Q  P   Y  P  G   A  P  H  H   S  S  Y   V  H  L
151 CGGCCGGCGC GACCCACAAG CCCACCCGCC CACAGCCACC GCGACTTCCA
    R  P  A  R   P  T  S   P  P  A   H  S  H  R   D  F  Q
201 GCCGGTGCTC CACCTGGTTG CGCTCAACAG CCCCCTGTCA GGCGGCATGC
     P  V  L   H  L  V  A   L  N  S   P  L  S   G  G  M  R
251 GGGGCATCCG CGGGGCCGAC TTCCAGTGCT TCCAGCAGGC GCGGGCCGTG
     G  I  R   G  A  D   F  Q  C  F   Q  Q  A   R  A  V
301 GGGCTGGCGG GCACCTTCCG CGCCTTCCTG TCCTCGCGCC TGCAGGACCT
    G  L  A  G   T  F  R   A  F  L   S  S  R  L   Q  D  L
351 GTACAGCATC GTGCGCCGTG CCGACCGCGC AGCCGTGCCC ATCGTCAACC
     Y  S  I   V  R  R  A   D  R  A   A  V  P   I  V  N  L
401 TCAAGGACGA GCTGCTGTTT CCCAGCTGGG AGGCTCTGTT CTCAGGCTCT
     K  D  E   L  L  F   P  S  W  E   A  L  F   S  G  S
451 GAGGGTCCGC TGAAGCCCGG GGCACGCATC TTCTCCTTTG ACGGCAAGGA
    E  G  P  L   K  P  G   A  R  I   F  S  F  D   G  K  D
501 CGTCCTGAGG CACCCCACCT GGCCCCAGAA GAGCGTGTGG CATGGCTCGG
     V  L  R   H  P  T  W   P  Q  K   S  V  W   H  G  S  D
551 ACCCCAACGG GCGCAGGCTG ACCGAGAGCT ACTGTGAGAC GTGGCGGACG
     P  N  G   R  R  L   T  E  S  Y   C  E  T   W  R  T
601 GAGGCTCCCT CGGCCACGGG CCAGGCCTCC TCGCTGCTGG GGGGCAGGCT
    E  A  P  S   A  T  G   Q  A  S   S  L  L  G   G  R  L
651 CCTGGGGCAG AGTGCCGCGA GCTGCCATCA CGCCTACATC GTGCTCTGCA
     L  G  Q   S  A  A  S   C  H  H   A  Y  I   V  L  C  I
701 TTGAGAACAG CTTCATGACT GCCTCCAAGT AG      [SEQ ID NO:1]
     E  N  S   F  M  T   A  S  K  *         [SEQ ID NO:2]
```

FIG. 5A

Neostatin-7 Human DNA sequence

```
  1 CTGCACGACA GCAACCCCTA CCCGCGGCGG GAGCACCCCC ACCCCACCGC
 51 GCGGCCCTGG CGGGCAGATG ACATCCTGGC CAGCCCCCCT CGCCTGCCCG
101 AGCCCCAGCC CTACCCCGGA GCCCCGCACC ACAGCTCCTA CGTGCACCTG
151 CGGCCGGCGC GACCCACAAG CCCACCCGCC CACAGCCACC GCGACTTCCA
201 GCCGGTGCTC CACCTGGTTG CGCTCAACAG CCCCCTGTCA GGCGGCATGC
251 GGGGCATCCG CGGGGCCGAC TTCCAGTGCT TCCAGCAGGC GCGGGCCGTG
301 GGGCTGGCGG GCACCTTCCG CGCCTTCCTG TCCTCGCGCC TGCAGGACCT
351 GTACAGCATC GTGCGCCGTG CCGACCGCGC AGCCGTGCCC ATCGTCAACC
401 TCAAGGACGA GCTGCTGTTT CCCAGCTGGG AGGCTCTGTT CTCAGGCTCT
451 GAGGGTCCGC TGAAGCCCGG GGCACGCATC TTCTCCTTTG ACGGCAAGGA
501 CGTCCTGAGG CACCCCACCT GGCCCCAGAA GAGCGTGTGG CATGGCTCGG
551 ACCCCAACGG GCGCAGGCTG ACCGAGAGCT ACTGTGAGAC GTGGCGGACG
601 GAGGCTCCCT CGGCCACGGG CCAGGCCTCC TCGCTGCTGG GGGGCAGGCT
651 CCTGGGGCAG AGTGCCGCGA GCTGCCATCA CGCCTACATC GTGCTCTGCA
701 TTGAGAACAG CTTCATGACT GCCTCCAAGT AG   [SEQ ID NO:1]
```

FIG. 5B

Neostatin-7 protein sequence

```
LHDSNPYPRREHPHPTARPWRADDILASPPRLPEPQPYPGAPHHSSY
VHLRPARPTSPPAHSHRDFQPVLHLVALNSPLSGGMRGIRGADFQCFQQARAVGLAGT
FRAFLSSRLQDLYSIVRRADRAAVPIVNLKDELLFPSWEALFSGSEGPLKPGARIFSF
DGKDVLRHPTWPQKSVWHGSDPNGRRLTESYCETWRTEAPSATGQASSLLGGRLLGQS
AASCHHAYIVLCIENSFMTASK  [SEQ ID NO:2]
```

FIG. 5C

Human neostatin-14 Human DNA/protein sequence

```
  1 TACGTGCACC TGCGGCCGGC GCGACCCACA AGCCCACCCG CCCACAGCCA
     Y  V  H  L   R  P  A   R  P  T   S  P  P  A   H  S  H

 51 CCGCGACTTC CAGCCGGTGC TCCACCTGGT TGCGCTCAAC AGCCCCCTGT
     R  D  F   Q  P  V  L   H  L  V   A  L  N   S  P  L  S

101 CAGGCGGCAT GCGGGGCATC CGCGGGGCCG ACTTCCAGTG CTTCCAGCAG
       G  G  M   R  G  I   R  G  A  D   F  Q  C   F  Q  Q

151 GCGCGGGCCG TGGGGCTGGC GGGCACCTTC CGCGCCTTCC TGTCCTCGCG
     A  R  A  V   G  L  A   G  T  F   R  A  F  L   S  S  R

201 CCTGCAGGAC CTGTACAGCA TCGTGCGCCG TGCCGACCGC GCAGCCGTGC
     L  Q  D   L  Y  S  I   V  R  R   A  D  R   A  A  V  P

251 CCATCGTCAA CCTCAAGGAC GAGCTGCTGT TTCCCAGCTG GGAGGCTCTG
       I  V  N   L  K  D   E  L  L  F   P  S  W   E  A  L

301 TTCTCAGGCT CTGAGGGTCC GCTGAAGCCC GGGGCACGCA TCTTCTCCTT
     F  S  G  S   E  G  P   L  K  P   G  A  R  I   F  S  F

351 TGACGGCAAG GACGTCCTGA GGCACCCCAC CTGGCCCCAG AAGAGCGTGT
     D  G  K   D  V  L  R   H  P  T   W  P  Q   K  S  V  W

401 GGCATGGCTC GGACCCCAAC GGGCGCAGGC TGACCGAGAG CTACTGTGAG
       H  G  S   D  P  N   G  R  R  L   T  E  S   Y  C  E

451 ACGTGGCGGA CGGAGGCTCC CTCGGCCACG GGCCAGGCCT CCTCGCTGCT
     T  W  R  T   E  A  P   S  A  T   G  Q  A  S   S  L  L

501 GGGGGGCAGG CTCCTGGGGC AGAGTGCCGC GAGCTGCCAT CACGCCTACA
     G  G  R   L  L  G  Q   S  A  A   S  C  H   H  A  Y  I

551 TCGTGCTCTG CATTGAGAAC AGCTTCATGA CTGCCTCCAA GTAG
       V  L  C   I  E  N   S  F  M  T   A  S  K   *
```

[SEQ ID NO: 3]
[SEQ ID NO: 4]

FIG. 6A

Neostatin-14 human DNA sequence

```
  1 TACGTGCACC TGCGGCCGGC GCGACCCACA AGCCCACCCG CCCACAGCCA
 51 CCGCGACTTC CAGCCGGTGC TCCACCTGGT TGCGCTCAAC AGCCCCCTGT
101 CAGGCGGCAT GCGGGGCATC CGCGGGGCCG ACTTCCAGTG CTTCCAGCAG
151 GCGCGGGCCG TGGGGCTGGC GGGCACCTTC CGCGCCTTCC TGTCCTCGCG
201 CCTGCAGGAC CTGTACAGCA TCGTGCGCCG TGCCGACCGC GCAGCCGTGC
251 CCATCGTCAA CCTCAAGGAC GAGCTGCTGT TTCCCAGCTG GGAGGCTCTG
301 TTCTCAGGCT CTGAGGGTCC GCTGAAGCCC GGGGCACGCA TCTTCTCCTT
351 TGACGGCAAG GACGTCCTGA GGCACCCCAC CTGGCCCCAG AAGAGCGTGT
401 GGCATGGCTC GGACCCCAAC GGGCGCAGGC TGACCGAGAG CTACTGTGAG
451 ACGTGGCGGA CGGAGGCTCC CTCGGCCACG GGCCAGGCCT CCTCGCTGCT
501 GGGGGGCAGG CTCCTGGGGC AGAGTGCCGC GAGCTGCCAT CACGCCTACA
551 TCGTGCTCTG CATTGAGAAC AGCTTCATGA CTGCCTCCAA GTAG
    [SEQ ID NO:3]
```

FIG. 6B

Neostatin-14 Human protein sequence

YVHLRPARPTSPPAHSHRDFQPVLHLVALNSPLSGGMRGIRGADFQCFQQARAVGLAG
TFRAFLSSRLQDLYSIVRRADRAAVPIVNLKDELLFPSWEALFSGSEGPLKPGARIFS
FDGKDVLRHPTWPQKSVWHGSDPNGRRLTESYCETWRTEAPSATGQASSLLGGRLLGQ
SAASCHHAYIVLCIENSFMTASK [SEQ ID NO:4]

FIG. 6C

MMP-7 Human DNA/protein sequence

```
  1 ATGCGACTCA CCGTGCTGTG TGCTGTGTGC CTGCTGCCTG GCAGCCTGGC
     M  R  L  T   V  L  C   A  V  C   L  L  P  G   S  L  A

 51 CCTGCCGCTG CCTCAGGAGG CGGGAGGCAT GAGTGAGCTA CAGTGGGAAC
     L  P  L   P  Q  E  A   G  G  M   S  E  L   Q  W  E  Q

101 AGGCTCAGGA CTATCTCAAG AGATTTTATC TCTATGACTC AGAAACAAAA
      A  Q  D   Y  L  K   R  F  Y  L   Y  D  S   E  T  K

151 AATGCCAACA GTTTAGAAGC CAAACTCAAG GAGATGCAAA AATTCTTTGG
     N  A  N  S   L  E  A   K  L  K   E  M  Q  K   F  F  G

201 CCTACCTATA ACTGGAATGT TAAACTCCCG CGTCATAGAA ATAATGCAGA
     L  P  I   T  G  M  L   N  S  R   V  I  E   I  M  Q  K

251 AGCCCAGATG TGGAGTGCCA GATGTTGCAG AATACTCACT ATTTCCAAAT
      P  R  C   G  V  P   D  V  A  E   Y  S  L   F  P  N

301 AGCCCAAAAT GGACTTCCAA AGTGGTCACC TACAGGATCG TATCATATAC
     S  P  K  W   T  S  K   V  V  T   Y  R  I  V   S  Y  T

351 TCGAGACTTA CCGCATATTA CAGTGGATCG ATTAGTGTCA AAGGCTTTAA
     R  D  L   P  H  I  T   V  D  R   L  V  S   K  A  L  N

401 ACATGTGGGG CAAAGAGATC CCCCTGCATT TCAGGAAAGT TGTATGGGGA
      M  W  G   K  E  I   P  L  H  F   R  K  V   V  W  G

451 ACTGCTGACA TCATGATTGG CTTTGCGCGA GGAGCTCATG GGGACTCCTA
     T  A  D  I   M  I  G   F  A  R   G  A  H  G   D  S  Y

501 CCCATTTGAT GGGCCAGGAA ACACGCTGGC TCATGCCTTT GCGCCTGGGA
      P  F  D   G  P  G  N   T  L  A   H  A  F   A  P  G  T

551 CAGGTCTCGG AGGAGATGCT CACTTCGATG AGGATGAACG CTGGACGGAT
      G  L  G   G  D  A   H  F  D  E   D  E  R   W  T  D

601 GGTAGCAGTC TAGGGATTAA CTTCCTGTAT GCTGCAACTC ATGAACTTGG
     G  S  S  L   G  I  N   F  L  Y   A  A  T  H   E  L  G

651 CCATTCTTTG GGTATGGGAC ATTCCTCTGA TCCTAATGCA GTGATGTATC
     H  S  L   G  M  G  H   S  S  D   P  N  A   V  M  Y  P

701 CAACCTATGG AAATGGAGAT CCCCAAAATT TTAAACTTTC CCAGGATGAT
      T  Y  G   N  G  D   P  Q  N  F   K  L  S   Q  D  D

751 ATTAAAGGCA TTCAGAAACT ATATGGAAAG AGAAGTAATT CAAGAAAGAA
     I  K  G  I   Q  K  L   Y  G  K   R  S  N  S   R  K  K

801 ATAG              [SEQ ID NO:5]
      *               [SEQ ID NO:6]
```

FIG. 7A

MMP-7 Human DNA sequence

```
  1 ATGCGACTCA CCGTGCTGTG TGCTGTGTGC CTGCTGCCTG GCAGCCTGGC
 51 CCTGCCGCTG CCTCAGGAGG CGGGAGGCAT GAGTGAGCTA CAGTGGGAAC
101 AGGCTCAGGA CTATCTCAAG AGATTTTATC TCTATGACTC AGAAACAAAA
151 AATGCCAACA GTTTAGAAGC CAAACTCAAG GAGATGCAAA AATTCTTTGG
201 CCTACCTATA ACTGGAATGT TAAACTCCCG CGTCATAGAA ATAATGCAGA
251 AGCCCAGATG TGGAGTGCCA GATGTTGCAG AATACTCACT ATTTCCAAAT
301 AGCCCAAAAT GGACTTCCAA AGTGGTCACC TACAGGATCG TATCATATAC
351 TCGAGACTTA CCGCATATTA CAGTGGATCG ATTAGTGTCA AAGGCTTTAA
401 ACATGTGGGG CAAAGAGATC CCCCTGCATT TCAGGAAAGT TGTATGGGGA
451 ACTGCTGACA TCATGATTGG CTTTGCGCGA GGAGCTCATG GGGACTCCTA
501 CCCATTTGAT GGGCCAGGAA ACACGCTGGC TCATGCCTTT GCGCCTGGGA
551 CAGGTCTCGG AGGAGATGCT CACTTCGATG AGGATGAACG CTGGACGGAT
601 GGTAGCAGTC TAGGGATTAA CTTCCTGTAT GCTGCAACTC ATGAACTTGG
651 CCATTCTTTG GGTATGGGAC ATTCCTCTGA TCCTAATGCA GTGATGTATC
701 CAACCTATGG AAATGGAGAT CCCCAAAATT TTAAACTTTC CCAGGATGAT
751 ATTAAAGGCA TTCAGAAACT ATATGGAAAG AGAAGTAATT CAAGAAAGAA
801 ATAG  [SEQ ID NO:5]
```

FIG. 7B

MMP-7 human protein

MRLTVLCAVCLLPGSLALPLPQEAGGMSELQWEQAQDYLKRFYL
YDSETKNANSLEAKLKEMQKFFGLPITGMLNSRVIEIMQKPRCGVPDVAEYSLFPNSP
KWTSKVVTYRIVSYTRDLPHITVDRLVSKALNMWGKEIPLHFRKVVWGTADIMIGFAR
GAHGDSYPFDGPGNTLAHAFAPGTGLGGDAHFDEDERWTDGSSLGINFLYAATHELGH
SLGMGHSSDPNAVMYPTYGNGDPQNFKLSQDDIKGIQKLYGKRSNSRKK
[SEQ ID NO:6]

FIG. 7C

MMP-14 human DNA/protein sequence

```
  1 ATGTCTCCCG CCCCAAGACC CCCCCGTTGT CTCCTGCTCC CCCTGCTCAC
     M  S  P  A   P  R  P   P  R  C   L  L  L  P   L  L  T
 51 GCTCGGCACC GCGCTCGCCT CCCTCGGCTC GGCCCAAAGC AGCAGCTTCA
     L  G  T   A  L  A  S   L  G  S   A  Q  S   S  S  F  S
101 GCCCCGAAGC CTGGCTACAG CAATATGGCT ACCTGCCTCC CGGGGACCTA
     P  E  A   W  L  Q   Q  Y  G  Y   L  P  P   G  D  L
151 CGTACCCACA CACAGCGCTC ACCCCAGTCA CTCTCAGCGG CCATCGCTGC
     R  T  H  T   Q  R  S   P  Q  S   L  S  A  A   I  A  A
201 CATGCAGAAG TTTTACGGCT TGCAAGTAAC AGGCAAAGCT GATGCAGACA
     M  Q  K   F  Y  G  L   Q  V  T   G  K  A   D  A  D  T
251 CCATGAAGGC CATGAGGCGC CCCCGATGTG GTGTTCCAGA CAAGTTTGGG
     M  K  A   M  R  R   P  R  C  G   V  P  D   K  F  G
301 GCTGAGATCA AGGCCAATGT TCGAAGGAAG CGCTACGCCA TCCAGGGTCT
     A  E  I  K   A  N  V   R  R  K   R  Y  A  I   Q  G  L
351 CAAATGGCAA CATAATGAAA TCACTTTCTG CATCCAGAAT TACACCCCCA
     K  W  Q   H  N  E  I   T  F  C   I  Q  N   Y  T  P  K
401 AGGTGGGCGA GTATGCCACA TACGAGGCCA TTCGCAAGGC GTTCCGCGTG
     V  G  E   Y  A  T   Y  E  A  I   R  K  A   F  R  V
451 TGGGAGAGTG CCACACCACT GCGCTTCCGC GAGGTGCCCT ATGCCTACAT
     W  E  S  A   T  P  L   R  F  R   E  V  P  Y   A  Y  I
501 CCGTGAGGGC CATGAGAAGC AGGCCGACAT CATGATCTTC TTTGCCGAGG
     R  E  G   H  E  K  Q   A  D  I   M  I  F   F  A  E  G
551 GCTTCCATGG CGACAGCACG CCCTTCGATG GTGAGGGCGG CTTCCTGGCC
     F  H  G   D  S  T   P  F  D  G   E  G  G   F  L  A
601 CATGCCTACT TCCCAGGCCC CAACATTGGA GGAGACACCC ACTTTGACTC
     H  A  Y  F   P  G  P   N  I  G   G  D  T  H   F  D  S
651 TGCCGAGCCT TGGACTGTCA GGAATGAGGA TCTGAATGGA AATGACATCT
     A  E  P   W  T  V  R   N  E  D   L  N  G   N  D  I  F
701 TCCTGGTGGC TGTGCACGAG CTGGGCCATG CCCTGGGGCT CGAGCATTCC
     L  V  A   V  H  E   L  G  H  A   L  G  L   E  H  S
751 AGTGACCCCT CGGCCATCAT GGCACCCTTT TACCAGTGGA TGGACACGGA
     S  D  P  S   A  I  M   A  P  F   Y  Q  W  M   D  T  E
```

FIG. 8A-1

```
801  GAATTTTGTG CTGCCCGATG ATGACCGCCG GGGCATCCAG CAACTTTATG
      N  F  V   L  P  D  D   D  R  R   G  I  Q   Q  L  Y  G

851  GGGGTGAGTC AGGGTTCCCC ACCAAGATGC CCCCTCAACC CAGGACTACC
      G  E  S   G  F  P   T  K  M  P   P  Q  P   R  T  T

901  TCCCGGCCTT CTGTTCCTGA TAAACCCAAA AACCCCACCT ATGGGCCCAA
     S  R  P  S  V  P  D   K  P  K   N  P  T  Y   G  P  N

951  CATCTGTGAC GGGAACTTTG ACACCGTGGC CATGCTCCGA GGGGAGATGT
      I  C  D   G  N  F  D   T  V  A   M  L  R   G  E  M  F

1001 TTGTCTTCAA GGAGCGCTGG TTCTGGCGGG TGAGGAATAA CCAAGTGATG
      V  F  K   E  R  W   F  W  R  V   R  N  N   Q  V  M

1051 GATGGATACC CAATGCCCAT TGGCCAGTTC TGGCGGGGCC TGCCTGCGTC
     D  G  Y  P   M  P  I   G  Q  F   W  R  G  L   P  A  S

1101 CATCAACACT GCCTACGAGA GGAAGGATGG CAAATTCGTC TTCTTCAAAG
      I  N  T   A  Y  E  R   K  D  G   K  F  V   F  F  K  G

1151 GAGACAAGCA TTGGGTGTTT GATGAGGCGT CCCTGGAACC TGGCTACCCC
      D  K  H   W  V  F   D  E  A  S   L  E  P   G  Y  P

1201 AAGCACATTA AGGAGCTGGG CCGAGGGCTG CCTACCGACA AGATTGATGC
     K  H  I  K   E  L  G   R  G  L   P  T  D  K   I  D  A

1251 TGCTCTCTTC TGGATGCCCA ATGGAAAGAC CTACTTCTTC CGTGGAAACA
      A  L  F   W  M  P  N   G  K  T   Y  F  F   R  G  N  K

1301 AGTACTACCG TTTCAACGAA GAGCTCAGGG CAGTGGATAG CGAGTACCCC
      Y  Y  R   F  N  E   E  L  R  A   V  D  S   E  Y  P

1351 AAGAACATCA AAGTCTGGGA AGGGATCCCT GAGTCTCCCA GAGGGTCATT
     K  N  I  K   V  W  E   G  I  P   E  S  P  R   G  S  F

1401 CATGGGCAGC GATGAAGTCT TCACTTACTT CTACAAGGGG AACAAATACT
      M  G  S   D  E  V  F   T  Y  F   Y  K  G   N  K  Y  W

1451 GGAAATTCAA CAACCAGAAG CTGAAGGTAG AACCGGGCTA CCCCAAGTCA
      K  F  N   N  Q  K   L  K  V  E   P  G  Y   P  K  S

1501 GCCCTGAGGG ACTGGATGGG CTGCCCATCG GGAGGCCGGC CGGATGAGGG
     A  L  R  D   W  M  G   C  P  S   G  G  R  P   D  E  G

1551 GACTGAGGAG GAGACGGAGG TGATCATCAT TGAGGTGGAC GAGGAGGGCG
      T  E  E   E  T  E  V   I  I  I   E  V  D   E  E  G  G

1601 GCGGGGCGGT GAGCGCGGCT GCCGTGGTGC TGCCCGTGCT GCTGCTGCTC
      G  A  V   S  A  A   A  V  V  L   P  V  L   L  L  L
```

FIG. 8A-2

```
1651 CTGGTGCTGG CGGTGGGCCT TGCAGTCTTC TTCTTCAGAC GCCATGGGAC
      L  V  L  A   V  G  L   A  V  F   F  F  R  R   H  G  T

1701 CCCCAGGCGA CTGCTCTACT GCCAGCGTTC CCTGCTGGAC AAGGTCTGA
      P  R  R   L  L  Y  C   Q  R  S   L  L  D   K  V  *

[SEQ ID NO: 7]
[SEQ ID NO: 8]
```

FIG. 8A-3

MMP-14 human DNA sequence

```
   1 ATGTCTCCCG CCCCAAGACC CCCCCGTTGT CTCCTGCTCC CCCTGCTCAC
  51 GCTCGGCACC GCGCTCGCCT CCCTCGGCTC GGCCCAAAGC AGCAGCTTCA
 101 GCCCCGAAGC CTGGCTACAG CAATATGGCT ACCTGCCTCC CGGGGACCTA
 151 CGTACCCACA CACAGCGCTC ACCCCAGTCA CTCTCAGCGG CCATCGCTGC
 201 CATGCAGAAG TTTTACGGCT TGCAAGTAAC AGGCAAAGCT GATGCAGACA
 251 CCATGAAGGC CATGAGGCGC CCCCGATGTG GTGTTCCAGA CAAGTTTGGG
 301 GCTGAGATCA AGGCCAATGT TCGAAGGAAG CGCTACGCCA TCCAGGGTCT
 351 CAAATGGCAA CATAATGAAA TCACTTTCTG CATCCAGAAT TACACCCCCA
 401 AGGTGGGCGA GTATGCCACA TACGAGGCCA TTCGCAAGGC GTTCCGCGTG
 451 TGGGAGAGTG CCACACCACT GCGCTTCCGC GAGGTGCCCT ATGCCTACAT
 501 CCGTGAGGGC CATGAGAAGC AGGCCGACAT CATGATCTTC TTTGCCGAGG
 551 GCTTCCATGG CGACAGCACG CCCTTCGATG GTGAGGGCGG CTTCCTGGCC
 601 CATGCCTACT TCCCAGGCCC CAACATTGGA GGAGACACCC ACTTTGACTC
 651 TGCCGAGCCT TGGACTGTCA GGAATGAGGA TCTGAATGGA AATGACATCT
 701 TCCTGGTGGC TGTGCACGAG CTGGGCCATG CCCTGGGGCT CGAGCATTCC
 751 AGTGACCCCT CGGCCATCAT GGCACCCTTT TACCAGTGGA TGGACACGGA
 801 GAATTTTGTG CTGCCCGATG ATGACCGCCG GGGCATCCAG CAACTTTATG
 851 GGGGTGAGTC AGGGTTCCCC ACCAAGATGC CCCCTCAACC CAGGACTACC
 901 TCCCGGCCTT CTGTTCCTGA TAAACCCAAA AACCCCACCT ATGGGCCCAA
 951 CATCTGTGAC GGGAACTTTG ACACCGTGGC CATGCTCCGA GGGGAGATGT
1001 TTGTCTTCAA GGAGCGCTGG TTCTGGCGGG TGAGGAATAA CCAAGTGATG
1051 GATGGATACC CAATGCCCAT TGGCCAGTTC TGGCGGGGCC TGCCTGCGTC
1101 CATCAACACT GCCTACGAGA GGAAGGATGG CAAATTCGTC TTCTTCAAAG
1151 GAGACAAGCA TTGGGTGTTT GATGAGGCGT CCCTGGAACC TGGCTACCCC
1201 AAGCACATTA AGGAGCTGGG CCGAGGGCTG CCTACCGACA AGATTGATGC
1251 TGCTCTCTTC TGGATGCCCA ATGGAAAGAC CTACTTCTTC CGTGGAAACA
1301 AGTACTACCG TTTCAACGAA GAGCTCAGGG CAGTGGATAG CGAGTACCCC
1351 AAGAACATCA AAGTCTGGGA AGGGATCCCT GAGTCTCCCA GAGGGTCATT
1401 CATGGGCAGC GATGAAGTCT TCACTTACTT CTACAAGGGG AACAAATACT
1451 GGAAATTCAA CAACCAGAAG CTGAAGGTAG AACCGGGCTA CCCCAAGTCA
1501 GCCCTGAGGG ACTGGATGGG CTGCCCATCG GGAGGCCGGC CGGATGAGGG
1551 GACTGAGGAG GAGACGGAGG TGATCATCAT TGAGGTGGAC GAGGAGGGCG
1601 GCGGGGCGGT GAGCGCGGCT GCCGTGGTGC TGCCCGTGCT GCTGCTGCTC
1651 CTGGTGCTGG CGGTGGGCCT TGCAGTCTTC TTCTTCAGAC GCCATGGGAC
1701 CCCCAGGCGA CTGCTCTACT GCCAGCGTTC CCTGCTGGAC AAGGTCTGA
```

[SEQ ID NO:7]

FIG. 8B

MMP-14 human protein sequence
MSPAPRPPRCLLLPLLTLGTALASLGSAQSSSFSPEAWLQQYGY
LPPGDLRTHTQRSPQSLSAAIAAMQKFYGLQVTGKADADTMKAMRRPRCGVPDKFGAE
IKANVRRKRYAIQGLKWQHNEITFCIQNYTPKVGEYATYEAIRKAFRVWESATPLRFR
EVPYAYIREGHEKQADIMIFFAEGFHGDSTPFDGEGGFLAHAYFPGPNIGGDTHFDSA
EPWTVRNEDLNGNDIFLVAVHELGHALGLEHSSDPSAIMAPFYQWMDTENFVLPDDDR
RGIQQLYGGESGFPTKMPPQPRTTSRPSVPDKPKNPTYGPNICDGNFDTVAMLRGEMF
VFKERWFWRVRNNQVMDGYPMPIGQFWRGLPASINTAYERKDGKFVFFKGDKHWVFDE
ASLEPGYPKHIKELGRGLPTDKIDAALFWMPNGKTYFFRGNKYYRFNEELRAVDSEYP
KNIKVWEGIPESPRGSFMGSDEVFTYFYKGNKYWKFNNQKLKVEPGYPKSALRDWMGC
PSGGRPDEGTEEETEVIIIEVDEEGGGAVSAAAVVLPVLLLLLVLAVGLAVFFFRRHG
TPRRLLYCQRSLLDKV [SEQ ID NO:8]

FIG. 8C

SEQUENCE LISTING

<160> NUMBER OF SEQ ID NOS: 15

<210> SEQ ID NO 1
<211> LENGTH: 732

```
<212> TYPE: DNA
<213> ORGANISM: Homo sapiens
<220> FEATURE:
<221> NAME/KEY: CDS
<222> LOCATION: (1)...(729)

<400> SEQUENCE: 1

ctg cac gac agc aac ccc tac ccg cgg cgg gag cac ccc cac ccc acc       48
Leu His Asp Ser Asn Pro Tyr Pro Arg Arg Glu His Pro His Pro Thr
 1               5                  10                  15

gcg cgg ccc tgg cgg gca gat gac atc ctg gcc agc ccc cct cgc ctg       96
Ala Arg Pro Trp Arg Ala Asp Asp Ile Leu Ala Ser Pro Pro Arg Leu
            20                  25                  30

ccc gag ccc cag ccc tac ccc gga gcc ccg cac cac agc tcc tac gtg      144
Pro Glu Pro Gln Pro Tyr Pro Gly Ala Pro His His Ser Ser Tyr Val
        35                  40                  45

cac ctg cgg ccg gcg cga ccc aca agc cca ccc gcc cac agc cac cgc      192
His Leu Arg Pro Ala Arg Pro Thr Ser Pro Pro Ala His Ser His Arg
    50                  55                  60

gac ttc cag ccg gtg ctc cac ctg gtt gcg ctc aac agc ccc ctg tca      240
Asp Phe Gln Pro Val Leu His Leu Val Ala Leu Asn Ser Pro Leu Ser
 65                  70                  75                  80

ggc ggc atg cgg ggc atc cgc ggg gcc gac ttc cag tgc ttc cag cag      288
Gly Gly Met Arg Gly Ile Arg Gly Ala Asp Phe Gln Cys Phe Gln Gln
                85                  90                  95

gcg cgg gcc gtg ggg ctg gcg ggc acc ttc cgc gcc ttc ctg tcc tcg      336
Ala Arg Ala Val Gly Leu Ala Gly Thr Phe Arg Ala Phe Leu Ser Ser
            100                 105                 110

cgc ctg cag gac ctg tac agc atc gtg cgc cgt gcc gac cgc gca gcc      384
Arg Leu Gln Asp Leu Tyr Ser Ile Val Arg Arg Ala Asp Arg Ala Ala
        115                 120                 125

gtg ccc atc gtc aac ctc aag gac gag ctg ctg ttt ccc agc tgg gag      432
Val Pro Ile Val Asn Leu Lys Asp Glu Leu Leu Phe Pro Ser Trp Glu
    130                 135                 140

gct ctg ttc tca ggc tct gag ggt ccg ctg aag ccc ggg gca cgc atc      480
Ala Leu Phe Ser Gly Ser Glu Gly Pro Leu Lys Pro Gly Ala Arg Ile
145                 150                 155                 160

ttc tcc ttt gac ggc aag gac gtc ctg agg cac ccc acc tgg ccc cag      528
Phe Ser Phe Asp Gly Lys Asp Val Leu Arg His Pro Thr Trp Pro Gln
                165                 170                 175

aag agc gtg tgg cat ggc tcg gac ccc aac ggg cgc agg ctg acc gag      576
Lys Ser Val Trp His Gly Ser Asp Pro Asn Gly Arg Arg Leu Thr Glu
            180                 185                 190

agc tac tgt gag acg tgg cgg acg gag gct ccc tcg gcc acg ggc cag      624
Ser Tyr Cys Glu Thr Trp Arg Thr Glu Ala Pro Ser Ala Thr Gly Gln
        195                 200                 205

gcc tcc tcg ctg ctg ggg ggc agg ctc ctg ggg cag agt gcc gcg agc      672
Ala Ser Ser Leu Leu Gly Gly Arg Leu Leu Gly Gln Ser Ala Ala Ser
    210                 215                 220

tgc cat cac gcc tac atc gtg ctc tgc att gag aac agc ttc atg act      720
Cys His His Ala Tyr Ile Val Leu Cys Ile Glu Asn Ser Phe Met Thr
225                 230                 235                 240

gcc tcc aag tag                                                      732
Ala Ser Lys


<210> SEQ ID NO 2
<211> LENGTH: 243
<212> TYPE: PRT
<213> ORGANISM: Homo sapiens

<400> SEQUENCE: 2

Leu His Asp Ser Asn Pro Tyr Pro Arg Arg Glu His Pro His Pro Thr
```

-continued

```
 1               5                   10                  15

Ala Arg Pro Trp Arg Ala Asp Asp Ile Leu Ala Ser Pro Pro Arg Leu
            20                  25                  30

Pro Glu Pro Gln Pro Tyr Pro Gly Ala Pro His His Ser Ser Tyr Val
        35                  40                  45

His Leu Arg Pro Ala Arg Pro Thr Ser Pro Pro Ala His Ser His Arg
    50                  55                  60

Asp Phe Gln Pro Val Leu His Leu Val Ala Leu Asn Ser Pro Leu Ser
65                  70                  75                  80

Gly Gly Met Arg Gly Ile Arg Gly Ala Asp Phe Gln Cys Phe Gln Gln
                85                  90                  95

Ala Arg Ala Val Gly Leu Ala Gly Thr Phe Arg Ala Phe Leu Ser Ser
            100                 105                 110

Arg Leu Gln Asp Leu Tyr Ser Ile Val Arg Arg Ala Asp Arg Ala Ala
        115                 120                 125

Val Pro Ile Val Asn Leu Lys Asp Glu Leu Leu Phe Pro Ser Trp Glu
    130                 135                 140

Ala Leu Phe Ser Gly Ser Glu Gly Pro Leu Lys Pro Gly Ala Arg Ile
145                 150                 155                 160

Phe Ser Phe Asp Gly Lys Asp Val Leu Arg His Pro Thr Trp Pro Gln
                165                 170                 175

Lys Ser Val Trp His Gly Ser Asp Pro Asn Gly Arg Arg Leu Thr Glu
            180                 185                 190

Ser Tyr Cys Glu Thr Trp Arg Thr Glu Ala Pro Ser Ala Thr Gly Gln
        195                 200                 205

Ala Ser Ser Leu Leu Gly Gly Arg Leu Leu Gly Gln Ser Ala Ala Ser
    210                 215                 220

Cys His His Ala Tyr Ile Val Leu Cys Ile Glu Asn Ser Phe Met Thr
225                 230                 235                 240

Ala Ser Lys


<210> SEQ ID NO 3
<211> LENGTH: 594
<212> TYPE: DNA
<213> ORGANISM: Homo sapiens
<220> FEATURE:
<221> NAME/KEY: CDS
<222> LOCATION: (1)...(591)

<400> SEQUENCE: 3

tac gtg cac ctg cgg ccg gcg cga ccc aca agc cca ccc gcc cac agc       48
Tyr Val His Leu Arg Pro Ala Arg Pro Thr Ser Pro Pro Ala His Ser
 1               5                   10                  15

cac cgc gac ttc cag ccg gtg ctc cac ctg gtt gcg ctc aac agc ccc       96
His Arg Asp Phe Gln Pro Val Leu His Leu Val Ala Leu Asn Ser Pro
            20                  25                  30

ctg tca ggc ggc atg cgg ggc atc cgc ggg gcc gac ttc cag tgc ttc      144
Leu Ser Gly Gly Met Arg Gly Ile Arg Gly Ala Asp Phe Gln Cys Phe
        35                  40                  45

cag cag gcg cgg gcc gtg ggg ctg gcg ggc acc ttc cgc gcc ttc ctg      192
Gln Gln Ala Arg Ala Val Gly Leu Ala Gly Thr Phe Arg Ala Phe Leu
    50                  55                  60

tcc tcg cgc ctg cag gac ctg tac agc atc gtg cgc cgt gcc gac cgc      240
Ser Ser Arg Leu Gln Asp Leu Tyr Ser Ile Val Arg Arg Ala Asp Arg
 65                  70                  75                  80

gca gcc gtg ccc atc gtc aac ctc aag gac gag ctg ctg ttt ccc agc      288
Ala Ala Val Pro Ile Val Asn Leu Lys Asp Glu Leu Leu Phe Pro Ser
                85                  90                  95
```

-continued

```
tgg gag gct ctg ttc tca ggc tct gag ggt ccg ctg aag ccc ggg gca      336
Trp Glu Ala Leu Phe Ser Gly Ser Glu Gly Pro Leu Lys Pro Gly Ala
            100                 105                 110

cgc atc ttc tcc ttt gac ggc aag gac gtc ctg agg cac ccc acc tgg      384
Arg Ile Phe Ser Phe Asp Gly Lys Asp Val Leu Arg His Pro Thr Trp
        115                 120                 125

ccc cag aag agc gtg tgg cat ggc tcg gac ccc aac ggg cgc agg ctg      432
Pro Gln Lys Ser Val Trp His Gly Ser Asp Pro Asn Gly Arg Arg Leu
    130                 135                 140

acc gag agc tac tgt gag acg tgg cgg acg gag gct ccc tcg gcc acg      480
Thr Glu Ser Tyr Cys Glu Thr Trp Arg Thr Glu Ala Pro Ser Ala Thr
145                 150                 155                 160

ggc cag gcc tcc tcg ctg ctg ggg ggc agg ctc ctg ggg cag agt gcc      528
Gly Gln Ala Ser Ser Leu Leu Gly Gly Arg Leu Leu Gly Gln Ser Ala
                165                 170                 175

gcg agc tgc cat cac gcc tac atc gtg ctc tgc att gag aac agc ttc      576
Ala Ser Cys His His Ala Tyr Ile Val Leu Cys Ile Glu Asn Ser Phe
            180                 185                 190

atg act gcc tcc aag tag                                              594
Met Thr Ala Ser Lys
        195


<210> SEQ ID NO 4
<211> LENGTH: 197
<212> TYPE: PRT
<213> ORGANISM: Homo sapiens

<400> SEQUENCE: 4

Tyr Val His Leu Arg Pro Ala Arg Pro Thr Ser Pro Pro Ala His Ser
 1               5                  10                  15

His Arg Asp Phe Gln Pro Val Leu His Leu Val Ala Leu Asn Ser Pro
            20                  25                  30

Leu Ser Gly Gly Met Arg Gly Ile Arg Gly Ala Asp Phe Gln Cys Phe
        35                  40                  45

Gln Gln Ala Arg Ala Val Gly Leu Ala Gly Thr Phe Arg Ala Phe Leu
    50                  55                  60

Ser Ser Arg Leu Gln Asp Leu Tyr Ser Ile Val Arg Arg Ala Asp Arg
65                  70                  75                  80

Ala Ala Val Pro Ile Val Asn Leu Lys Asp Glu Leu Leu Phe Pro Ser
                85                  90                  95

Trp Glu Ala Leu Phe Ser Gly Ser Glu Gly Pro Leu Lys Pro Gly Ala
            100                 105                 110

Arg Ile Phe Ser Phe Asp Gly Lys Asp Val Leu Arg His Pro Thr Trp
        115                 120                 125

Pro Gln Lys Ser Val Trp His Gly Ser Asp Pro Asn Gly Arg Arg Leu
    130                 135                 140

Thr Glu Ser Tyr Cys Glu Thr Trp Arg Thr Glu Ala Pro Ser Ala Thr
145                 150                 155                 160

Gly Gln Ala Ser Ser Leu Leu Gly Gly Arg Leu Leu Gly Gln Ser Ala
                165                 170                 175

Ala Ser Cys His His Ala Tyr Ile Val Leu Cys Ile Glu Asn Ser Phe
            180                 185                 190

Met Thr Ala Ser Lys
        195


<210> SEQ ID NO 5
<211> LENGTH: 804
<212> TYPE: DNA
```

<213> ORGANISM: Homo sapiens
<220> FEATURE:
<221> NAME/KEY: CDS
<222> LOCATION: (1)...(801)

<400> SEQUENCE: 5

```
atg cga ctc acc gtg ctg tgt gct gtg tgc ctg ctg cct ggc agc ctg       48
Met Arg Leu Thr Val Leu Cys Ala Val Cys Leu Leu Pro Gly Ser Leu
 1               5                  10                  15

gcc ctg ccg ctg cct cag gag gcg gga ggc atg agt gag cta cag tgg       96
Ala Leu Pro Leu Pro Gln Glu Ala Gly Gly Met Ser Glu Leu Gln Trp
            20                  25                  30

gaa cag gct cag gac tat ctc aag aga ttt tat ctc tat gac tca gaa      144
Glu Gln Ala Gln Asp Tyr Leu Lys Arg Phe Tyr Leu Tyr Asp Ser Glu
        35                  40                  45

aca aaa aat gcc aac agt tta gaa gcc aaa ctc aag gag atg caa aaa      192
Thr Lys Asn Ala Asn Ser Leu Glu Ala Lys Leu Lys Glu Met Gln Lys
    50                  55                  60

ttc ttt ggc cta cct ata act gga atg tta aac tcc cgc gtc ata gaa      240
Phe Phe Gly Leu Pro Ile Thr Gly Met Leu Asn Ser Arg Val Ile Glu
 65                  70                  75                  80

ata atg cag aag ccc aga tgt gga gtg cca gat gtt gca gaa tac tca      288
Ile Met Gln Lys Pro Arg Cys Gly Val Pro Asp Val Ala Glu Tyr Ser
                85                  90                  95

cta ttt cca aat agc cca aaa tgg act tcc aaa gtg gtc acc tac agg      336
Leu Phe Pro Asn Ser Pro Lys Trp Thr Ser Lys Val Val Thr Tyr Arg
            100                 105                 110

atc gta tca tat act cga gac tta ccg cat att aca gtg gat cga tta      384
Ile Val Ser Tyr Thr Arg Asp Leu Pro His Ile Thr Val Asp Arg Leu
        115                 120                 125

gtg tca aag gct tta aac atg tgg ggc aaa gag atc ccc ctg cat ttc      432
Val Ser Lys Ala Leu Asn Met Trp Gly Lys Glu Ile Pro Leu His Phe
    130                 135                 140

agg aaa gtt gta tgg gga act gct gac atc atg att ggc ttt gcg cga      480
Arg Lys Val Val Trp Gly Thr Ala Asp Ile Met Ile Gly Phe Ala Arg
145                 150                 155                 160

gga gct cat ggg gac tcc tac cca ttt gat ggg cca gga aac acg ctg      528
Gly Ala His Gly Asp Ser Tyr Pro Phe Asp Gly Pro Gly Asn Thr Leu
                165                 170                 175

gct cat gcc ttt gcg cct ggg aca ggt ctc gga gga gat gct cac ttc      576
Ala His Ala Phe Ala Pro Gly Thr Gly Leu Gly Gly Asp Ala His Phe
            180                 185                 190

gat gag gat gaa cgc tgg acg gat ggt agc agt cta ggg att aac ttc      624
Asp Glu Asp Glu Arg Trp Thr Asp Gly Ser Ser Leu Gly Ile Asn Phe
        195                 200                 205

ctg tat gct gca act cat gaa ctt ggc cat tct ttg ggt atg gga cat      672
Leu Tyr Ala Ala Thr His Glu Leu Gly His Ser Leu Gly Met Gly His
    210                 215                 220

tcc tct gat cct aat gca gtg atg tat cca acc tat gga aat gga gat      720
Ser Ser Asp Pro Asn Ala Val Met Tyr Pro Thr Tyr Gly Asn Gly Asp
225                 230                 235                 240

ccc caa aat ttt aaa ctt tcc cag gat gat att aaa ggc att cag aaa      768
Pro Gln Asn Phe Lys Leu Ser Gln Asp Asp Ile Lys Gly Ile Gln Lys
                245                 250                 255

cta tat gga aag aga agt aat tca aga aag aaa tag                      804
Leu Tyr Gly Lys Arg Ser Asn Ser Arg Lys Lys
            260                 265
```

<210> SEQ ID NO 6
<211> LENGTH: 267
<212> TYPE: PRT
<213> ORGANISM: Homo sapiens

<400> SEQUENCE: 6

```
Met Arg Leu Thr Val Leu Cys Ala Val Cys Leu Leu Pro Gly Ser Leu
 1               5                  10                  15

Ala Leu Pro Leu Pro Gln Glu Ala Gly Gly Met Ser Glu Leu Gln Trp
            20                  25                  30

Glu Gln Ala Gln Asp Tyr Leu Lys Arg Phe Tyr Leu Tyr Asp Ser Glu
        35                  40                  45

Thr Lys Asn Ala Asn Ser Leu Glu Ala Lys Leu Lys Glu Met Gln Lys
    50                  55                  60

Phe Phe Gly Leu Pro Ile Thr Gly Met Leu Asn Ser Arg Val Ile Glu
65                  70                  75                  80

Ile Met Gln Lys Pro Arg Cys Gly Val Pro Asp Val Ala Glu Tyr Ser
                85                  90                  95

Leu Phe Pro Asn Ser Pro Lys Trp Thr Ser Lys Val Val Thr Tyr Arg
            100                 105                 110

Ile Val Ser Tyr Thr Arg Asp Leu Pro His Ile Thr Val Asp Arg Leu
        115                 120                 125

Val Ser Lys Ala Leu Asn Met Trp Gly Lys Glu Ile Pro Leu His Phe
    130                 135                 140

Arg Lys Val Val Trp Gly Thr Ala Asp Ile Met Ile Gly Phe Ala Arg
145                 150                 155                 160

Gly Ala His Gly Asp Ser Tyr Pro Phe Asp Gly Pro Gly Asn Thr Leu
                165                 170                 175

Ala His Ala Phe Ala Pro Gly Thr Gly Leu Gly Gly Asp Ala His Phe
            180                 185                 190

Asp Glu Asp Glu Arg Trp Thr Asp Gly Ser Ser Leu Gly Ile Asn Phe
        195                 200                 205

Leu Tyr Ala Ala Thr His Glu Leu Gly His Ser Leu Gly Met Gly His
    210                 215                 220

Ser Ser Asp Pro Asn Ala Val Met Tyr Pro Thr Tyr Gly Asn Gly Asp
225                 230                 235                 240

Pro Gln Asn Phe Lys Leu Ser Gln Asp Asp Ile Lys Gly Ile Gln Lys
                245                 250                 255

Leu Tyr Gly Lys Arg Ser Asn Ser Arg Lys Lys
            260                 265
```

<210> SEQ ID NO 7
<211> LENGTH: 1749
<212> TYPE: DNA
<213> ORGANISM: Homo sapiens
<220> FEATURE:
<221> NAME/KEY: CDS
<222> LOCATION: (1)...(1746)

<400> SEQUENCE: 7

```
atg tct ccc gcc cca aga ccc ccc cgt tgt ctc ctg ctc ccc ctg ctc       48
Met Ser Pro Ala Pro Arg Pro Pro Arg Cys Leu Leu Leu Pro Leu Leu
 1               5                  10                  15

acg ctc ggc acc gcg ctc gcc tcc ctc ggc tcg gcc caa agc agc agc       96
Thr Leu Gly Thr Ala Leu Ala Ser Leu Gly Ser Ala Gln Ser Ser Ser
            20                  25                  30

ttc agc ccc gaa gcc tgg cta cag caa tat ggc tac ctg cct ccc ggg      144
Phe Ser Pro Glu Ala Trp Leu Gln Gln Tyr Gly Tyr Leu Pro Pro Gly
        35                  40                  45

gac cta cgt acc cac aca cag cgc tca ccc cag tca ctc tca gcg gcc      192
Asp Leu Arg Thr His Thr Gln Arg Ser Pro Gln Ser Leu Ser Ala Ala
    50                  55                  60
```

```
atc gct gcc atg cag aag ttt tac ggc ttg caa gta aca ggc aaa gct      240
Ile Ala Ala Met Gln Lys Phe Tyr Gly Leu Gln Val Thr Gly Lys Ala
 65                  70                  75                  80

gat gca gac acc atg aag gcc atg agg cgc ccc cga tgt ggt gtt cca      288
Asp Ala Asp Thr Met Lys Ala Met Arg Arg Pro Arg Cys Gly Val Pro
                 85                  90                  95

gac aag ttt ggg gct gag atc aag gcc aat gtt cga agg aag cgc tac      336
Asp Lys Phe Gly Ala Glu Ile Lys Ala Asn Val Arg Arg Lys Arg Tyr
            100                 105                 110

gcc atc cag ggt ctc aaa tgg caa cat aat gaa atc act ttc tgc atc      384
Ala Ile Gln Gly Leu Lys Trp Gln His Asn Glu Ile Thr Phe Cys Ile
        115                 120                 125

cag aat tac acc ccc aag gtg ggc gag tat gcc aca tac gag gcc att      432
Gln Asn Tyr Thr Pro Lys Val Gly Glu Tyr Ala Thr Tyr Glu Ala Ile
    130                 135                 140

cgc aag gcg ttc cgc gtg tgg gag agt gcc aca cca ctg cgc ttc cgc      480
Arg Lys Ala Phe Arg Val Trp Glu Ser Ala Thr Pro Leu Arg Phe Arg
145                 150                 155                 160

gag gtg ccc tat gcc tac atc cgt gag ggc cat gag aag cag gcc gac      528
Glu Val Pro Tyr Ala Tyr Ile Arg Glu Gly His Glu Lys Gln Ala Asp
                165                 170                 175

atc atg atc ttc ttt gcc gag ggc ttc cat ggc gac agc acg ccc ttc      576
Ile Met Ile Phe Phe Ala Glu Gly Phe His Gly Asp Ser Thr Pro Phe
            180                 185                 190

gat ggt gag ggc ggc ttc ctg gcc cat gcc tac ttc cca ggc ccc aac      624
Asp Gly Glu Gly Gly Phe Leu Ala His Ala Tyr Phe Pro Gly Pro Asn
        195                 200                 205

att gga gga gac acc cac ttt gac tct gcc gag cct tgg act gtc agg      672
Ile Gly Gly Asp Thr His Phe Asp Ser Ala Glu Pro Trp Thr Val Arg
    210                 215                 220

aat gag gat ctg aat gga aat gac atc ttc ctg gtg gct gtg cac gag      720
Asn Glu Asp Leu Asn Gly Asn Asp Ile Phe Leu Val Ala Val His Glu
225                 230                 235                 240

ctg ggc cat gcc ctg ggg ctc gag cat tcc agt gac ccc tcg gcc atc      768
Leu Gly His Ala Leu Gly Leu Glu His Ser Ser Asp Pro Ser Ala Ile
                245                 250                 255

atg gca ccc ttt tac cag tgg atg gac acg gag aat ttt gtg ctg ccc      816
Met Ala Pro Phe Tyr Gln Trp Met Asp Thr Glu Asn Phe Val Leu Pro
            260                 265                 270

gat gat gac cgc cgg ggc atc cag caa ctt tat ggg ggt gag tca ggg      864
Asp Asp Asp Arg Arg Gly Ile Gln Gln Leu Tyr Gly Gly Glu Ser Gly
        275                 280                 285

ttc ccc acc aag atg ccc cct caa ccc agg act acc tcc cgg cct tct      912
Phe Pro Thr Lys Met Pro Pro Gln Pro Arg Thr Thr Ser Arg Pro Ser
    290                 295                 300

gtt cct gat aaa ccc aaa aac ccc acc tat ggg ccc aac atc tgt gac      960
Val Pro Asp Lys Pro Lys Asn Pro Thr Tyr Gly Pro Asn Ile Cys Asp
305                 310                 315                 320

ggg aac ttt gac acc gtg gcc atg ctc cga ggg gag atg ttt gtc ttc     1008
Gly Asn Phe Asp Thr Val Ala Met Leu Arg Gly Glu Met Phe Val Phe
                325                 330                 335

aag gag cgc tgg ttc tgg cgg gtg agg aat aac caa gtg atg gat gga     1056
Lys Glu Arg Trp Phe Trp Arg Val Arg Asn Asn Gln Val Met Asp Gly
            340                 345                 350

tac cca atg ccc att ggc cag ttc tgg cgg ggc ctg cct gcg tcc atc     1104
Tyr Pro Met Pro Ile Gly Gln Phe Trp Arg Gly Leu Pro Ala Ser Ile
        355                 360                 365

aac act gcc tac gag agg aag gat ggc aaa ttc gtc ttc ttc aaa gga     1152
Asn Thr Ala Tyr Glu Arg Lys Asp Gly Lys Phe Val Phe Phe Lys Gly
    370                 375                 380
```

```
gac aag cat tgg gtg ttt gat gag gcg tcc ctg gaa cct ggc tac ccc      1200
Asp Lys His Trp Val Phe Asp Glu Ala Ser Leu Glu Pro Gly Tyr Pro
385                 390                 395                 400

aag cac att aag gag ctg ggc cga ggg ctg cct acc gac aag att gat      1248
Lys His Ile Lys Glu Leu Gly Arg Gly Leu Pro Thr Asp Lys Ile Asp
                405                 410                 415

gct gct ctc ttc tgg atg ccc aat gga aag acc tac ttc ttc cgt gga      1296
Ala Ala Leu Phe Trp Met Pro Asn Gly Lys Thr Tyr Phe Phe Arg Gly
            420                 425                 430

aac aag tac tac cgt ttc aac gaa gag ctc agg gca gtg gat agc gag      1344
Asn Lys Tyr Tyr Arg Phe Asn Glu Glu Leu Arg Ala Val Asp Ser Glu
        435                 440                 445

tac ccc aag aac atc aaa gtc tgg gaa ggg atc cct gag tct ccc aga      1392
Tyr Pro Lys Asn Ile Lys Val Trp Glu Gly Ile Pro Glu Ser Pro Arg
    450                 455                 460

ggg tca ttc atg ggc agc gat gaa gtc ttc act tac ttc tac aag ggg      1440
Gly Ser Phe Met Gly Ser Asp Glu Val Phe Thr Tyr Phe Tyr Lys Gly
465                 470                 475                 480

aac aaa tac tgg aaa ttc aac aac cag aag ctg aag gta gaa ccg ggc      1488
Asn Lys Tyr Trp Lys Phe Asn Asn Gln Lys Leu Lys Val Glu Pro Gly
                485                 490                 495

tac ccc aag tca gcc ctg agg gac tgg atg ggc tgc cca tcg gga ggc      1536
Tyr Pro Lys Ser Ala Leu Arg Asp Trp Met Gly Cys Pro Ser Gly Gly
            500                 505                 510

cgg ccg gat gag ggg act gag gag gag acg gag gtg atc atc att gag      1584
Arg Pro Asp Glu Gly Thr Glu Glu Glu Thr Glu Val Ile Ile Ile Glu
        515                 520                 525

gtg gac gag gag ggc ggc ggg gcg gtg agc gcg gct gcc gtg gtg ctg      1632
Val Asp Glu Glu Gly Gly Gly Ala Val Ser Ala Ala Ala Val Val Leu
    530                 535                 540

ccc gtg ctg ctg ctg ctc ctg gtg ctg gcg gtg ggc ctt gca gtc ttc      1680
Pro Val Leu Leu Leu Leu Leu Val Leu Ala Val Gly Leu Ala Val Phe
545                 550                 555                 560

ttc ttc aga cgc cat ggg acc ccc agg cga ctg ctc tac tgc cag cgt      1728
Phe Phe Arg Arg His Gly Thr Pro Arg Arg Leu Leu Tyr Cys Gln Arg
                565                 570                 575

tcc ctg ctg gac aag gtc tga                                          1749
Ser Leu Leu Asp Lys Val
            580


<210> SEQ ID NO 8
<211> LENGTH: 582
<212> TYPE: PRT
<213> ORGANISM: Homo sapiens

<400> SEQUENCE: 8

Met Ser Pro Ala Pro Arg Pro Pro Arg Cys Leu Leu Leu Pro Leu Leu
 1               5                  10                  15

Thr Leu Gly Thr Ala Leu Ala Ser Leu Gly Ser Ala Gln Ser Ser Ser
            20                  25                  30

Phe Ser Pro Glu Ala Trp Leu Gln Gln Tyr Gly Tyr Leu Pro Pro Gly
        35                  40                  45

Asp Leu Arg Thr His Thr Gln Arg Ser Pro Gln Ser Leu Ser Ala Ala
    50                  55                  60

Ile Ala Ala Met Gln Lys Phe Tyr Gly Leu Gln Val Thr Gly Lys Ala
65                  70                  75                  80

Asp Ala Asp Thr Met Lys Ala Met Arg Arg Pro Arg Cys Gly Val Pro
                85                  90                  95

Asp Lys Phe Gly Ala Glu Ile Lys Ala Asn Val Arg Arg Lys Arg Tyr
```

-continued

```
            100                 105                 110

Ala Ile Gln Gly Leu Lys Trp Gln His Asn Glu Ile Thr Phe Cys Ile
        115                 120                 125

Gln Asn Tyr Thr Pro Lys Val Gly Glu Tyr Ala Thr Tyr Glu Ala Ile
    130                 135                 140

Arg Lys Ala Phe Arg Val Trp Glu Ser Ala Thr Pro Leu Arg Phe Arg
145                 150                 155                 160

Glu Val Pro Tyr Ala Tyr Ile Arg Glu Gly His Glu Lys Gln Ala Asp
                165                 170                 175

Ile Met Ile Phe Phe Ala Glu Gly Phe His Gly Asp Ser Thr Pro Phe
            180                 185                 190

Asp Gly Glu Gly Gly Phe Leu Ala His Ala Tyr Phe Pro Gly Pro Asn
        195                 200                 205

Ile Gly Gly Asp Thr His Phe Asp Ser Ala Glu Pro Trp Thr Val Arg
    210                 215                 220

Asn Glu Asp Leu Asn Gly Asn Asp Ile Phe Leu Val Ala Val His Glu
225                 230                 235                 240

Leu Gly His Ala Leu Gly Leu Glu His Ser Ser Asp Pro Ser Ala Ile
                245                 250                 255

Met Ala Pro Phe Tyr Gln Trp Met Asp Thr Glu Asn Phe Val Leu Pro
            260                 265                 270

Asp Asp Asp Arg Arg Gly Ile Gln Gln Leu Tyr Gly Gly Glu Ser Gly
        275                 280                 285

Phe Pro Thr Lys Met Pro Pro Gln Pro Arg Thr Thr Ser Arg Pro Ser
    290                 295                 300

Val Pro Asp Lys Pro Lys Asn Pro Thr Tyr Gly Pro Asn Ile Cys Asp
305                 310                 315                 320

Gly Asn Phe Asp Thr Val Ala Met Leu Arg Gly Glu Met Phe Val Phe
                325                 330                 335

Lys Glu Arg Trp Phe Trp Arg Val Arg Asn Asn Gln Val Met Asp Gly
            340                 345                 350

Tyr Pro Met Pro Ile Gly Gln Phe Trp Arg Gly Leu Pro Ala Ser Ile
        355                 360                 365

Asn Thr Ala Tyr Glu Arg Lys Asp Gly Lys Phe Val Phe Phe Lys Gly
    370                 375                 380

Asp Lys His Trp Val Phe Asp Glu Ala Ser Leu Glu Pro Gly Tyr Pro
385                 390                 395                 400

Lys His Ile Lys Glu Leu Gly Arg Gly Leu Pro Thr Asp Lys Ile Asp
                405                 410                 415

Ala Ala Leu Phe Trp Met Pro Asn Gly Lys Thr Tyr Phe Phe Arg Gly
            420                 425                 430

Asn Lys Tyr Tyr Arg Phe Asn Glu Glu Leu Arg Ala Val Asp Ser Glu
        435                 440                 445

Tyr Pro Lys Asn Ile Lys Val Trp Glu Gly Ile Pro Glu Ser Pro Arg
    450                 455                 460

Gly Ser Phe Met Gly Ser Asp Glu Val Phe Thr Tyr Phe Tyr Lys Gly
465                 470                 475                 480

Asn Lys Tyr Trp Lys Phe Asn Asn Gln Lys Leu Lys Val Glu Pro Gly
                485                 490                 495

Tyr Pro Lys Ser Ala Leu Arg Asp Trp Met Gly Cys Pro Ser Gly Gly
            500                 505                 510

Arg Pro Asp Glu Gly Thr Glu Glu Glu Thr Glu Val Ile Ile Ile Glu
        515                 520                 525
```

-continued

```
Val Asp Glu Glu Gly Gly Gly Ala Val Ser Ala Ala Ala Val Val Leu
    530                 535                 540

Pro Val Leu Leu Leu Leu Leu Val Leu Ala Val Gly Leu Ala Val Phe
545                 550                 555                 560

Phe Phe Arg Arg His Gly Thr Pro Arg Arg Leu Leu Tyr Cys Gln Arg
                565                 570                 575

Ser Leu Leu Asp Lys Val
            580
```

<210> SEQ ID NO 9
<211> LENGTH: 10
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: 2
<223> OTHER INFORMATION: Xaa = unknown amino acid

<400> SEQUENCE: 9

```
Leu Xaa Asp Ser Asn Pro Tyr Pro Arg Arg
 1               5                  10
```

<210> SEQ ID NO 10
<211> LENGTH: 33
<212> TYPE: DNA
<213> ORGANISM: Artificial Sequence
<220> FEATURE:
<223> OTHER INFORMATION: Primer

<400> SEQUENCE: 10
cctgaggcac ggaattccag gtggctgctt tcc 33

<210> SEQ ID NO 11
<211> LENGTH: 45
<212> TYPE: DNA
<213> ORGANISM: Artificial Sequence
<220> FEATURE:
<223> OTHER INFORMATION: Primer

<400> SEQUENCE: 11
gttccacatc accacgaatt ctatgtgcac ctgccgccag cccgc 45

<210> SEQ ID NO 12
<211> LENGTH: 36
<212> TYPE: DNA
<213> ORGANISM: Artificial Sequence
<220> FEATURE:
<223> OTHER INFORMATION: Primer

<400> SEQUENCE: 12
caccacagtt cctatgaatt cctgccgcca gcccgc 36

<210> SEQ ID NO 13
<211> LENGTH: 40
<212> TYPE: DNA
<213> ORGANISM: Artificial Sequence
<220> FEATURE:
<223> OTHER INFORMATION: Primer

<400> SEQUENCE: 13
ctgccaccct agctggcggc cgcctatttg gagaaagagg 40

<210> SEQ ID NO 14
<211> LENGTH: 10

-continued

<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: 1
<223> OTHER INFORMATION: Xaa = unknown amino acid

<400> SEQUENCE: 14

Xaa Val His Leu Arg Pro Ala Arg Pro Gly
1 5 10

<210> SEQ ID NO 15
<211> LENGTH: 319
<212> TYPE: PRT
<213> ORGANISM: Artificial Sequence
<220> FEATURE:
<223> OTHER INFORMATION: Synthetically generated peptide

<400> SEQUENCE: 15

Pro Gly Thr Met Gly Ala Ser Ser Gly Val Arg Leu Trp Ala Thr Arg
1 5 10 15

Gln Ala Met Leu Gly Gln Val His Glu Val Pro Glu Gly Trp Leu Ile
20 25 30

Phe Val Ala Glu Gln Glu Glu Leu Tyr Val Arg Val Gln Asn Gly Phe
35 40 45

Arg Lys Val Gln Leu Glu Ala Arg Thr Pro Leu Pro Arg Gly Thr Asp
50 55 60

Asn Glu Val Ala Ala Leu Gln Pro Pro Val Val Gln Leu His Asp Ser
65 70 75 80

Asn Pro Tyr Pro Arg Arg Glu His Pro His Pro Thr Ala Arg Pro Trp
85 90 95

Arg Ala Asp Asp Ile Leu Ala Ser Pro Pro Arg Leu Pro Glu Pro Gln
100 105 110

Pro Tyr Pro Gly Ala Pro His His Ser Ser Tyr Val His Leu Arg Pro
115 120 125

Ala Arg Pro Thr Ser Pro Pro Ala His Ser His Arg Asp Phe Gln Pro
130 135 140

Val Leu His Leu Val Ala Leu Asn Ser Pro Leu Ser Gly Gly Met Arg
145 150 155 160

Gly Ile Arg Gly Ala Asp Phe Gln Cys Phe Gln Gln Ala Arg Ala Val
165 170 175

Gly Leu Ala Gly Thr Phe Arg Ala Phe Leu Ser Ser Arg Leu Gln Asp
180 185 190

Leu Tyr Ser Ile Val Arg Arg Ala Asp Arg Ala Ala Val Pro Ile Val
195 200 205

Asn Leu Lys Asp Glu Leu Leu Phe Pro Ser Trp Glu Ala Leu Phe Ser
210 215 220

Gly Ser Glu Gly Pro Leu Lys Pro Gly Ala Arg Ile Phe Ser Phe Asp
225 230 235 240

Gly Lys Asp Val Leu Arg His Pro Thr Trp Pro Gln Lys Ser Val Trp
245 250 255

His Gly Ser Asp Pro Asn Gly Arg Arg Leu Thr Glu Ser Tyr Cys Glu
260 265 270

Thr Trp Arg Thr Glu Ala Pro Ser Ala Thr Gly Gln Ala Ser Ser Leu
275 280 285

-continued

```
Leu Gly Gly Arg Leu Leu Gly Gln Ser Ala Ala Ser Cys His His Ala
    290                 295                 300

Tyr Ile Val Leu Cys Ile Glu Asn Ser Phe Met Thr Ala Ser Lys
305                 310                 315
```

NEOSTATINS

CLAIM OF PRIORITY

This application is a CON of Ser. No. 11/965,411 Dec. 27, 2007 ABN which is a DIV of Ser. No. 11/346,490 Feb. 1, 2006 U.S. Pat. No. 7,662,945 which claims the benefit of 60/649,029 Feb. 1, 2005.

TECHNICAL FIELD

This invention relates to neostatin molecules and methods for their use.

BACKGROUND

Type XVIII collagen, a member of the multiplexin subfamily of collagens, is a proteoglycan composed largely of heparan sulfate side chains (Halfter et al., (1998) J. Biol. Chem. 273:25404-12). It is localized mainly in the perivascular regions around the blood vessels in the intestinal villi, choroids plexus, skin, liver and kidneys, and is present in adult and embryonic basal laminae (Kreuger et al., (2002) EMBO J. 21:6303-11). In ocular tissues, type XVIII collagen has been shown to be present in the retinal basal lamina, pigment epithelial basement lamina and periocular mesenchyme (Halfter et al., (1998) supra), as well as in the corneal epithelial basement membrane and in the stromal side of Descemet's membrane. Incisional wounds in mouse corneal tissue result in enhanced collagen XVIII mRNA and protein expression along the wound edges (Lin et al., (2001) Invest. Opthalmol. Vis. Sci. 42:2517-24; Kure et al., (2001) FEBS Lett. 508:187-90).

In vitro studies have shown that the hinge domain of type XVIII collagen, located between the association domain and the endostatin domain, is cleaved by proteases including elastase and/or cathepsin L to release endostatin, a 20 kDa peptide, from the carboxyl terminal of type XVIII collagen (Sasaki et al. (1998) EMBO J. 17:4249-56; Wen et al., (1999) Cancer Res. 59:6052-6; Felbor et al., (2000) EMBO J. 19:1187-94; Ferreras et al., (2000) FEBS Lett. 486:247-51).

Endostatin, has tumor-suppressing properties and potent anti-angiogenic activity (O'Reilly et al., (1997) Cell 88:277-85). Endostatin has been shown to inhibit cell migration, cell proliferation, decrease tumor size and enhance vascular endothelial cell apoptosis in vitro and in vivo (Chang et al., (2001) Curr. Opin. Opthalmol. 12:242-9; Colorado et al., (2000) Cancer Res. 60:2520-6; Marneros and Olsen, (2001) Matrix Biol. 20:337-45; Shichiri and Hirata, (2001) FASEB J. 15:1044-53). The mechanisms operative in the effect of endostatin on vascular endothelial cells have been intensively investigated and several endostatin-associated molecules have been isolated and characterized, including matrix metalloproteinase-2, integrin $\alpha V\beta 3$, VEGF receptor (KDR/flk-1), tropomyosin, glypican and laminin (Lee et al., (2002) FEBS Lett. 519:147-52; Rehn et al., (2001) Proc. Natl. Acad. Sci. USA 98:1024-9; Kim et al., (2000) Cancer Res. 60:5410-3; Kim et al., (2002) J. Biol. Chem. 277:27872-9; Javaherian et al., (2002) J. Biol. Chem. 277:45211-8). Endostatin binding to these cellular counterparts may facilitate the function of endostatin in vascular endothelial cell proliferation.

SUMMARY

The present invention is based on the discovery that proteolytic processing of type XVIII collagen in vivo in the eye generates fragments other than endostatin, and that these fragments have anti-angiogenic properties. Thus, the invention provides novel fragments of type XVIII collagen, and methods for their use in the treatment of medical and opthalmological disorders associated with angiogenesis, such as corneal, choroidal, uveal, and iris neovascularization, macular degeneration, diabetic retinopathy, and cancer, particularly cancers of the eye.

Thus, the invention includes isolated nucleic acid molecules encoding a polypeptide consisting of the sequence of SEQ ID NO:2 or 4, and isolated nucleic acid molecules encoding a polypeptide including at least a first portion consisting of the sequence of SEQ ID NO:2 or 4, and a second portion of non-collagen-derived sequence(s). The invention also includes vectors including the isolated nucleic acid sequences described herein, and host cells including those vectors.

In another aspect, the invention provides therapeutic compositions adapted for use in the eye. These therapeutic compositions include a pharmaceutically acceptable carrier and one or more of: polypeptides consisting of the sequence of SEQ ID NO:2 or 4; polypeptides including at least a first portion consisting of the sequence of SEQ ID NO:2 or 4, and a second portion including non-collagen-derived sequences; polypeptides consisting of the sequence of SEQ ID NO:2, 4, 6, or 8; polypeptides including at least a first portion consisting of the sequence of SEQ ID NO:2, 4, 6, or 8, and a second portion including non-collagen-derived sequences; and isolated nucleic acid molecules encoding a polypeptide described herein.

In a further aspect, the invention provides methods for treating patients who have an opthalmological disorder associated with angiogenesis, as described herein. The methods include administering to the patient a therapeutically effective amount of a composition described herein. The administering can be, e.g., topical or parenteral administration into the eye, e.g., including, but not limited to, local injection into or near the cornea, retina, vitreous, uvea, orbit, eyelid, conjunctiva, or iris.

In some embodiments, the opthalmological disorder is selected from the group consisting of eye cancer, age-related macular degeneration, retinopathy of prematurity, corneal graft rejection, glaucoma, diabetic retinopathy, wounds, age-related macular degeneration, herpetic and infectious keratitis, ocular ischemia, neovascular glaucoma, corneal, uveal and iris neovascularization, orbital and eyelid tumors, Stevens Johnson Syndrome, ocular cicatricial pemphigoid, and ocular surface diseases. In some embodiments, the opthalmological disorder is associated with corneal, retinal, choroidal, uveal, or iris neovascularization.

In another aspect, the invention provides methods for identifying candidate therapeutic compounds for the treatment of an opthalmological disorder associated with angiogenesis. The methods include obtaining a sample including one or more of an MMP-7 (e.g., SEQ ID NO:6) or MMP-14 (e.g., SEQ ID NO:8) polypeptide; contacting the sample with the test compound; and evaluating levels of MMP-7 and/or MMP-14 activity in the sample. An increase in levels of MMP-7 and/or MMP-14 activity in the sample indicates that the test compound is a candidate therapeutic compound for the treatment of an opthalmological disorder. The levels of MMP-7 and/or MMP-14 activity in the sample can be evaluated by measuring levels of neostatin-7 (e.g., SEQ ID NO:2) and/or neostatin-14 (e.g., SEQ ID NO:4) in the sample; an increase in neostatin-7 or -14 levels indicates an increase in levels of MMP-7 or -14 activity, respectively.

In some embodiments, the method further includes administering the candidate therapeutic compound to an animal model of an opthalmological disorder associated with angiogenesis, and monitoring the animal model for an effect of the candidate therapeutic compound on a parameter of the disorder, e.g., vascularisation, in the animal. A candidate therapeutic compound that causes an improvement in the parameter in the animal model is a therapeutic agent for the treatment of the disorder. In some embodiments, the methods include administering a therapeutically effective amount of the therapeutic agent to a subject in need of treatment for the disorder, thereby treating the disorder.

A neostatin polypeptide consists of a sequence that is at least about 85% identical to the amino acid sequence of SEQ ID NO:2 or 4, and has at anti-angiogenic activity. In some embodiments, a neostatin polypeptide is at least about 90%, 95%, 99%, or 100% identical to SEQ ID NO:2 or 4). Nucleic acid molecules encoding such polypeptides or proteins are collectively referred to as "neostatin nucleic acids." Neostatin molecules includes neostatin nucleic acids and polypeptides.

As used herein, the term "nucleic acid molecule" includes DNA molecules (e.g., a cDNA or genomic DNA) and RNA molecules (e.g., an mRNA) and analogs of the DNA or RNA generated, e.g., by the use of nucleotide analogs. The nucleic acid molecule can be single-stranded or double-stranded, but preferably is double-stranded DNA.

The term "isolated or purified nucleic acid molecule" includes nucleic acid molecules which are separated from other nucleic acid molecules that are present in the natural source of the nucleic acid. For example, in some embodiments, the isolated nucleic acid molecule can contain less than about 0.1 kb of 5' and/or 3' of the nucleotide sequences which naturally flank the nucleic acid molecule, e.g., in the mRNA. Moreover, an "isolated" nucleic acid molecule, such as a cDNA molecule, is substantially free of other cellular material, or culture medium when produced by recombinant techniques, or substantially free of chemical precursors or other chemicals when chemically synthesized.

As used herein, the term "stringent conditions" describes conditions for hybridization and washing. Stringent conditions as used herein are 0.5M sodium phosphate, 7% SDS at 65° C., followed by one or more washes at 0.2×SSC, 1% SDS at 65° C. See, e.g., *Current Protocols in Molecular Biology*, John Wiley & Sons, N.Y. (1989), 6.3.1-6.3.6.

As used herein, a "naturally-occurring" nucleic acid molecule refers to an RNA or DNA molecule having a nucleotide sequence that occurs in nature (e.g., encodes a natural protein).

A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted nonessential amino acid residue in a neostatin protein is preferably replaced with another amino acid residue from the same side chain family. Alternatively, in another embodiment, mutations can be introduced randomly along all or part of a neostatin coding sequence, such as by saturation mutagenesis, and the resultant mutants can be screened for neostatin biological activity to identify mutants that retain activity. Following mutagenesis, the encoded protein can be expressed recombinantly and the activity of the protein can be determined.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DESCRIPTION OF DRAWINGS

FIGS. 5A-5C illustrate the Human neostatin-7 human DNA/protein sequences, SEQ ID NOs:1 and 2.

FIGS. 6A-6C illustrate the Human neostatin-14 human DNA/protein sequences, SEQ ID NOs:3 and 4.

FIGS. 7A-7C illustrate the Human MMP-7 DNA/protein sequences, SEQ ID NOs:5 and 6.

FIGS. 8A-8C illustrate the Human MMP-14 DNA/protein sequences, SEQ ID NOs:7 and 8.

DETAILED DESCRIPTION

Figure 1A:
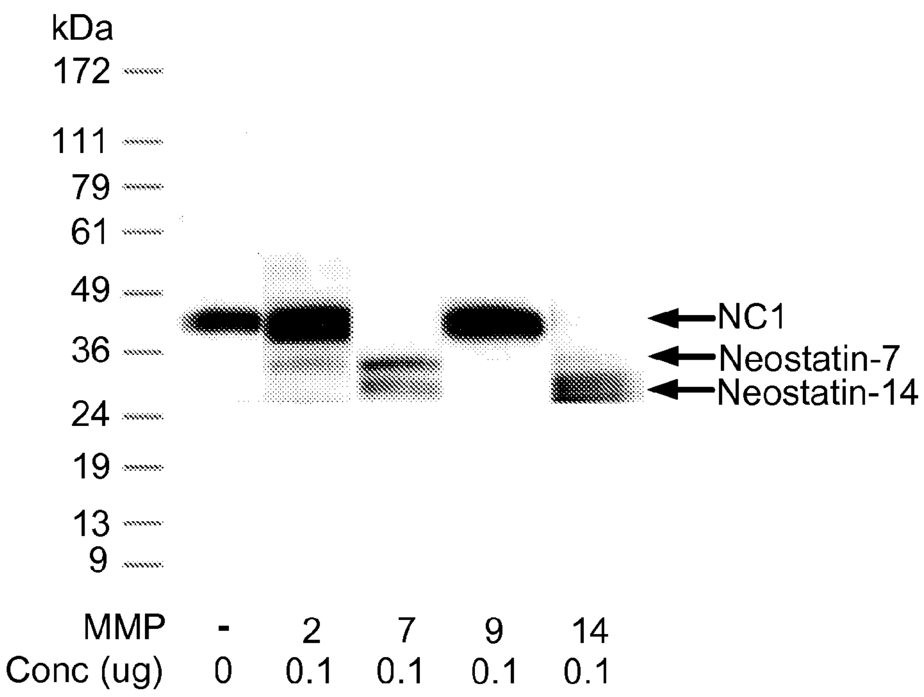
FIG. 1A is a reproduction of a Western blot showing fragments of the NC1 region of type XVIII collagen generated by cleavage with MMP-2, -7, -9 and -14, detected with anti-mouse endostatin antibodies.
Figure 1B:
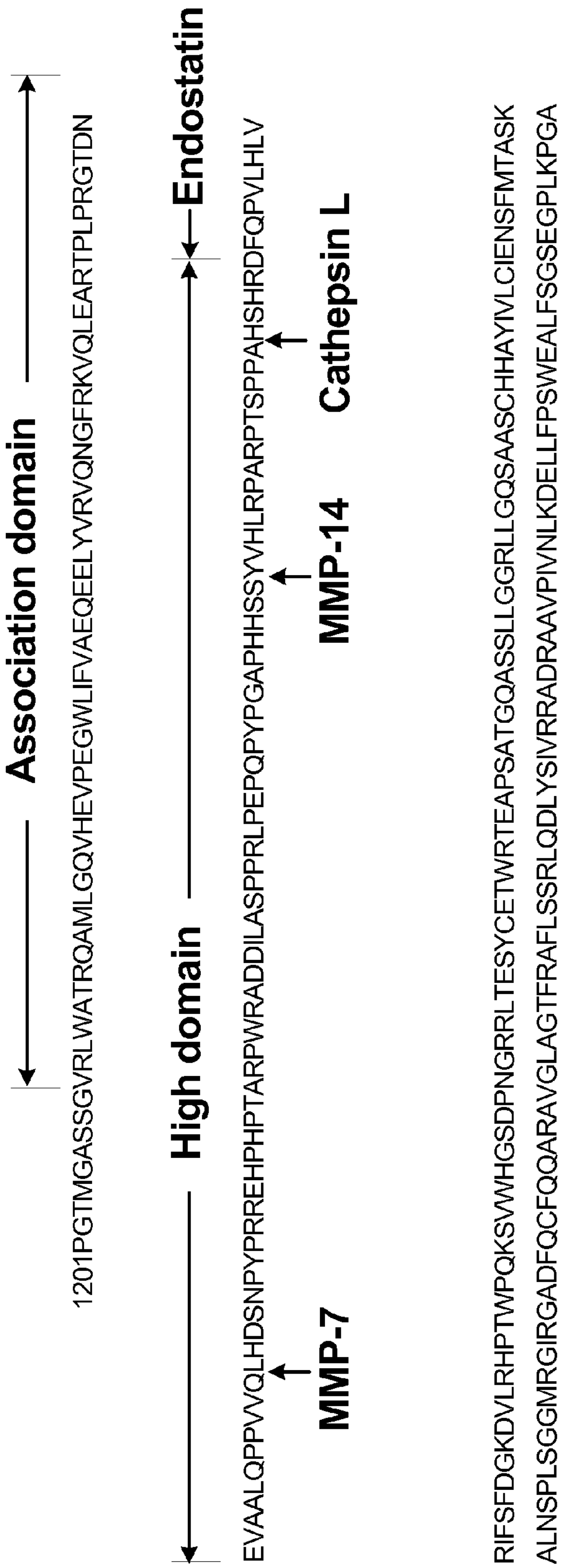
FIG. 1B is a diagram of collagen XVIII cleaved by MMP-7 and MMP-14. (x=unknown amino acid) (SEQ ID NO:15)

Neostatin-7, a C-terminal 28 kDa endostatin-spanning proteolytic fragment, is generated by proteolytic cleavage of matrix metalloproteinase matrilysin (MMP)-7 on type XVIII collagen (Lin et al., (2001) Invest. Opthalmol. Vis. Sci. 42:2517-24). A second member of the neostatin family of proteins, neostatin-14, generated by cleavage of collagen XVIII using MMP-14, is described herein. Murine recombinant neostatin and gene therapy were used to characterize the anti-angiogenic properties of these molecules. As described herein, murine recombinant neostatin-7 inhibits calf pulmonary artery endothelial cell proliferation, and gene therapy using microinjection of neostatin-7 or -14 naked DNA into the corneal stroma of mice results in significant reduction of bFGF-induced corneal neovascularization. Also as described herein, neostatin-7 and -14 have anti-angiogenic activity, and are therapeutically useful not only for the treatment of corneal and ocular neovascularization, e.g., in humans, but also for the treatment of benign and malignant tumors, e.g., eye tumors.

One of the matrix metalloproteinases (MMPs) expressed in the cornea during normal and wound-healing conditions, matrilysin (MMP-7), cleaves the NC1 hinge region of type XVIII collagen (this region is also referred to herein as "collagen XVIII/NC1") at a location upstream from the cathepsin L cleavage site to generate a member of the neostatin family, neostatin-7, an approximately 28 kDa endostatin-spanning fragment (Lin et al., (2001) supra). As reported herein, another MMP (MMP-14) also cleaves collagen XVIII/NC1 to produce a novel neostatin of about ~23 kDa neostatin (neostatin-14). The activity of MMP-7 and -14 on type XVIII collagen (and on the NC1 region of type XVIII collagen, in particular) generates neostatin-7 and -14, respectively, with specific 3-dimensional structural characteristics and specific glycosylation. The studies described herein determined that recombinant murine neostatin-7 (possibly lacking exact 3-dimensional and glycosylation characteristics of naturally-occurring neostatins) has anti-angiogenic activity. Also described herein is the use of therapy, e.g., gene or protein therapy, with MMP-7, MMP-14, neostatin-7, or neostatin-14 to treat neovascularization in the cornea, which provides a practical and effective alternative to using naturally derived or recombinant neostatins.

In the cornea, the balance between angiogenic and anti-angiogenic factors holds sway over the avascular milieu of the cornea and is governed by many variables. Injurious stimuli generate a multitude of responses aimed at the proteolysis of precursors to generate factors which tilt the balance towards the production or prevention of neovascularization. MMP-7 is up-regulated in wild-type animal wounding models, and an increased vascular response is seen in MMP-7 deficient littermates (Kure et al., (2003) Invest. Opthalmol. Vis. Sci. 44:137-44); MMP-14 is also expressed in the eye. As one theory, not meant to be limiting, MMP-7- and MMP-14-derived neostatins may be part of an array of factors that prevent new vessel formation ostensibly independent of endostatin. Thus, MMP-7 and -14 may have a role in the regulation of neovascularization and tumorigenesis, possibly by cleaving precursor molecules to produce anti-angiogenic molecules including, but not limited to, neostatin-7 and -14. The neostatins, MMP-7, and -14, provide new target molecules for the treatment of corneal and ocular angiogenic disorders as well as benign and malignant tumors.

Typically, the cleavage site for a protease involves residues both N- and C-terminal to the scissile bond (the unprimed and primed sides, respectively, with the cleavage site for a protease defined as P3-P2-P1-P1'-P2'-P3', with cleavage occurring between the P1 and P1' residues). MMP-7 has a substrate cleavage preference for a hydrophobic amino acid at P1', preferring either leucine or isoleucine (Woessner Jr. and Taplin, (1998) J. Biol. Chem. 263:16918-25; Turk et al., (2001) Nature Biotechnology 19:661-667). In type XVIII collagen, the data described herein demonstrates that active MMP-7 enzyme cleaves the 34-kDa NC1 region of type XVIII collagen. The resulting ~28-kDa fragment was subjected to N-terminal protein sequencing and was shown to have an N-terminal amino acid sequence of LxDSNPYPRR (SEQ ID NO:9), located in the hinge region of NC1 domain. A polyclonal antibody that can differentiate between neostatin-7 and neostatin-14 is also described herein. This antibody was raised against a highly conserved residue of neostatin-spanning peptides 1305-1326 of murine type XVIII collagen, which corresponds to peptides 1299-1320 of human type XVIII collagen. These peptide sequences of neostatin-7 are two residues upstream of the amino terminal end of neostatin-14.

The observations, described herein, that administration of neostatin-7 results in diminished serum-induced vascular endothelial cell proliferation in vitro, and that naked DNA injection of neostatin-7 and -14 inhibits bFGF induced corneal neovascularization in vivo, suggest that MMP-7 and/or -14 cleavage of type XVIII collagen may play a role in the regulation of angiogenesis via the production of neostatin-7 or -14. Thus, MMP-7, MMP-14, and the neostatins provide targets for the development of therapies to promote the maintenance of corneal avascularity during wound healing, as well as anti-angiogenic therapies to protect against the development of angiogenesis-dependent diseases such as ocular neovascular disorders and neoplasms.

Neostatin-7 and -14 Nucleic Acid Molecules

In one aspect, the invention provides isolated nucleic acid molecules that encode a neostatin polypeptide described herein, e.g., a neostatin-7 or -14 protein. Also included is a nucleic acid fragment suitable for use as a hybridization probe, which can be used, e.g., to identify a nucleic acid molecule encoding a polypeptide of the invention, and fragments suitable for use as primers, e.g., PCR primers for the amplification or mutation of neostatin nucleic acid molecules.

In some embodiments, an isolated neostatin nucleic acid molecule consists of the nucleotide sequence shown in SEQ ID NO:1 or 3.

In another embodiment, a neostatin nucleic acid molecule includes a nucleic acid molecule which is a complement of a sequence described herein. In some embodiments, a neostatin nucleic acid molecule is sufficiently complementary to a nucleotide sequence described herein that it can hybridize to the nucleotide sequence under stringent conditions, thereby forming a stable duplex.

In one embodiment, a neostatin isolated nucleic acid molecule includes a nucleotide sequence which is at least about 85% or more identical to the entire length of a nucleotide sequence shown in SEQ ID NO:1 or 3. In some embodiments, the nucleotide sequence is at least about 90%, 91%, 92%, 93%, 94%, 95%, 96%, 97%, 98%, 99% or 100% identical to SEQ ID NO:1 or 3.

Calculations of homology or sequence identity between sequences (the terms are used interchangeably herein) are performed as follows.

To determine the percent identity of two amino acid sequences, or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). The length of a reference sequence aligned for comparison purposes is at least 80% of the length of the reference sequence, and in some embodiments is at least 90% or 100%. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

For purposes of the present invention, the comparison of sequences and determination of percent identity between two sequences can be accomplished using a Blossum 62 scoring matrix with a gap penalty of 12, a gap extend penalty of 4, and a frameshift gap penalty of 5.

Also included herein are nucleic acid molecules that include only a portion of the nucleic acid sequence of SEQ ID NO:1 or 3. For example, such a nucleic acid molecule can include a fragment which can be used as a primer, e.g., to detect or amplify the sequence of SEQ ID NO:1 or 3.

Thus, neostatin probes and primers are provided. Typically a probe/primer is an isolated or purified oligonucleotide. The oligonucleotide typically includes a region of nucleotide sequence that hybridizes under stringent conditions to at least about 15 consecutive nucleotides of a sense or antisense sequence of SEQ ID NO:1 or 3. In some embodiments, the oligonucleotide comprises about 20, 25, 30, 35, 40, 45, 50, 55, 60, 65, or 75 consecutive nucleotides of SEQ ID NO:1 or 3.

In some embodiments, the nucleic acid is a probe which is at least 10, and less than 200 (typically less than about 100 or 50) base pairs in length. It should be identical, or differ by 1, or less than 1 in 5 or 10 bases, from a sequence disclosed herein. If alignment is needed for this comparison the sequences should be aligned for maximum homology. "Looped" out sequences from deletions or insertions, or mismatches, are considered differences.

In another embodiment a set of primers is provided, e.g., primers suitable for use in a PCR, which can be used to amplify a selected neostatin sequence. The primers should be at least 20 base pairs in length and less than about 100 base pairs in length. The primers should be identical, or differ by one base from a sequence disclosed herein or from a naturally occurring variant.

A nucleic acid fragment can encode an epitope-bearing region of a polypeptide described herein, e.g., an antigenic epitope specific to the neostatin, e.g., as described herein.

Also included herein are neostatin nucleic acid molecules that differ from the nucleotide sequence shown in SEQ ID NO:1 or 3. Such differences can be due to degeneracy of the genetic code (and result in a nucleic acid which encodes the same neostatin proteins as those encoded by the nucleotide sequence disclosed herein. In another embodiment, an isolated nucleic acid molecule of the invention has a nucleotide sequence encoding a protein having an amino acid sequence which differs, by at least 1, but less than 5, 10, 20, 50, or 100 amino acid residues that shown in SEQ ID NO:1 or 3. If alignment is needed for this comparison the sequences should be aligned for maximum homology. "Looped" out sequences from deletions or insertions, or mismatches, are considered differences.

Nucleic acids of the inventor can be chosen for having codons, which are preferred, or non preferred, for a particular expression system. For example, the nucleic acid can be one in which at least one codon, at preferably at least 10%, or 20% of the codons has been altered such that the sequence is optimized for expression in *E. coli*, yeast, human, insect, or CHO cells.

Nucleic acid variants can be naturally occurring, such as allelic variants (same locus), homologs (different locus), and orthologs (different organism) or can be non naturally occurring. Non-naturally occurring variants can be made by mutagenesis techniques, including those applied to polynucleotides, cells, or organisms. The variants can contain nucleotide substitutions, deletions, inversions and insertions. Variation can occur in either or both the coding and non-coding regions. The variations can produce both conservative and non-conservative amino acid substitutions (as compared in the encoded product).

In a preferred embodiment, the nucleic acid differs from that of SEQ ID NO: 1 or 3 as follows: by at least one but less than 10, 20, 30, or 40 nucleotides; at least one but less than 1%, 5%, 10% or 20% of the nucleotides in the subject nucleic acid. If necessary for this analysis the sequences should be aligned for maximum homology. "Looped" out sequences from deletions or insertions, or mismatches, are considered differences.

Neostatin-7 and -14 Polypeptides

Isolated Neostatin polypeptides are also described herein, as well as fragments thereof, e.g., for use as immunogens or antigens to raise or test (or more generally to bind) anti-neostatin antibodies. Neostatin polypeptides can be isolated from cells or tissue sources using standard protein purification techniques. Neostatin polypeptides or fragments thereof can be produced by recombinant DNA techniques or synthesized chemically. In some embodiments, the neostatin polypeptides consist of SEQ ID NO:2 or 4.

In some embodiments the neostatin polypeptides or fragments thereof are variants that differ from the corresponding sequence in SEQ ID NO:2 or 4, e.g., differ by at least one but by less than 15, 10 or 5 amino acid residues, or less than 20%, 15%, 10% or 5% of the residues. (If this comparison requires alignment the sequences should be aligned for maximum homology. "Looped" out sequences from deletions or insertions, or mismatches, are considered differences.) The differences are, preferably, differences or changes at a non essential residue or a conservative substitution. Such variants retain the anti-angiogenic activity of the neostatin protein, e.g., at least 50% of the activity as measured in an assay described herein.

In one embodiment, the protein includes an amino acid sequence that is at least 80%, e.g., about 85%, 90%, 95%, 98% or more homologous to SEQ ID NO:2 or 4.

In some embodiments the difference is at a non essential residue or is a conservative substitution, while in others the difference is at an essential residue or is a non conservative substitution.

Neostatin Chimeric or Fusion Proteins

Neostatin chimeric or fusion proteins are also described herein. As used herein, a neostatin "chimeric protein" or "fusion protein" includes a neostatin polypeptide linked to a non-neostatin polypeptide. A "non-neostatin polypeptide" refers to a polypeptide having an amino acid sequence corresponding to a protein which is not substantially homologous to the neostatin protein, e.g., a protein which is different from the neostatin protein, not a part of collagen XVIII, and which is derived from the same or a different organism. The non-neostatin polypeptide can be fused to the N-terminus or C-terminus of the neostatin polypeptide.

The fusion protein can include a moiety which has a high affinity for a ligand. For example, the fusion protein can be a GST-neostatin fusion protein in which the neostatin sequences are fused to the C-terminus of the GST sequences. Such fusion proteins can facilitate the purification of recombinant neostatin. Alternatively, the fusion protein can be a neostatin protein containing a heterologous signal sequence at its N-terminus. In certain host cells (e.g., mammalian host cells), expression and/or secretion of neostatin can be increased through use of a heterologous signal sequence.

In some embodiments, the fusion protein includes a cell-penetrating peptide sequence that facilitates delivery of neostatin to the intracellular space, e.g., HIV-derived TAT peptide, penetratins, transportans, or hCT derived cell-penetrating peptides, see, e.g., Caron et al., (2001) Mol. Ther. 3(3):310-8; Langel, *Cell-Penetrating Peptides: Processes and Applications* (CRC Press, Boca Raton Fla. 2002); El-Andaloussi et al., (2005) Curr Pharm Des. 11(28):3597-611; and Deshayes et al., (2005) Cell Mol Life Sci. 62(16):1839-49.

Fusion proteins can also include all or a part of a serum protein, e.g., an IgG constant region, or human serum albumin.

Variants of Neostatin Proteins

In another aspect, the invention also features variants of a neostatin polypeptide, e.g., which functions as an agonist (mimetics) or as an antagonist. Variants of the neostatin proteins can be generated by mutagenesis, e.g., discrete point mutation, the insertion or deletion of sequences or the truncation of a neostatin protein. An agonist of the neostatin proteins can retain substantially the same, or a subset, of the biological activities of the naturally occurring form of a neostatin protein. An antagonist of a neostatin protein can inhibit one or more of the activities of the naturally occurring form of the neostatin protein by, for example, competitively modulating a neostatin-mediated activity of a neostatin protein. Thus, specific biological effects can be elicited by treatment with a variant of limited function. Preferably, treatment of a subject with a variant having a subset of the biological activities of a naturally occurring form of the protein has fewer side effects in a subject relative to treatment with a naturally occurring form of a neostatin protein.

Active variants of a neostatin protein can be identified by screening libraries of mutants, e.g., point mutants, of a neostatin protein for agonist or antagonist activity. Methods for screening gene products of combinatorial libraries made by point mutations or truncation, and for screening cDNA libraries for gene products having a selected property, e.g., anti-angiogenic activity, are known in the art. Recursive ensemble mutagenesis (REM), a new technique which enhances the frequency of functional mutants in the libraries, can be used in combination with the screening assays to identify neostatin variants (Arkin and Yourvan (1992) *Proc. Natl. Acad. Sci.* USA 89:7811-7815; Delgrave et al. (1993) *Protein Engineering* 6:327-331).

Anti-Neostatin Antibodies

In another aspect, the invention provides an anti-neostatin antibody. The term "antibody" as used herein refers to an immunoglobulin molecule or immunologically active portion thereof, i.e., an antigen-binding portion. Examples of immunologically active portions of immunoglobulin molecules include F(ab) and $F(ab')_2$ fragments which can be generated by treating the antibody with an enzyme such as pepsin.

The antibody can be a polyclonal, monoclonal, recombinant, e.g., a chimeric or humanized, fully human, non-human, e.g., murine, or single chain antibody. In a preferred embodiment it has effector function and can fix complement. The antibody can be coupled to a toxin or imaging agent.

A full-length neostatin protein or antigenic peptide fragment of neostatin can be used as an immunogen or can be used to identify anti-neostatin antibodies made with other immunogens, e.g., cell extracts, and the like. The antigenic peptide of neostatin should include at least 8 amino acid residues of the amino acid sequence shown in SEQ ID NO:2 or 4 and encompass an epitope of neostatin, e.g., as described herein. Preferably, the antigenic peptide includes at least 10 amino acid residues, more preferably at least 15 amino acid residues, even more preferably at least 20 amino acid residues, and most preferably at least 30 amino acid residues.

Preferred epitopes encompassed by the antigenic peptide are regions of neostatin are located on the surface of the protein, e.g., hydrophilic regions, as well as regions with high antigenicity. For example, an Emini surface probability analysis of the human neostatin protein sequence can be used to indicate the regions that have a particularly high probability of being localized to the surface of the neostatin protein and are thus likely to constitute surface residues useful for targeting antibody production.

Chimeric, humanized, but most preferably, completely human antibodies are desirable for applications which include repeated administration, e.g., therapeutic treatment (and some diagnostic applications) of human patients.

The anti-neostatin antibody can be a single chain antibody. A single-chain antibody (scFV) may be engineered (see, for example, Colcher, D. et al. (1999) *Ann NY Acad Sci* 880:263-80; and Reiter, Y. (1996) *Clin Cancer Res* 2:245-52). The single chain antibody can be dimerized or multimerized to generate multivalent antibodies having specificities for different epitopes of the same target neostatin protein.

In a preferred embodiment, the antibody has reduced or no ability to bind an Fc receptor. For example, it is a isotype or subtype, fragment or other mutant, which does not support binding to an Fc receptor, e.g., it has a mutagenized or deleted Fc receptor binding region.

An anti-neostatin antibody (e.g., monoclonal antibody) can be used to isolate neostatin by standard techniques, such as affinity chromatography or immunoprecipitation. Moreover, an anti-neostatin antibody can be used to detect a neostatin protein (e.g., in a cellular lysate or cell supernatant) in order to evaluate the abundance and pattern of expression of the protein. Anti-neostatin antibodies can be used diagnostically to monitor protein levels in tissue as part of a clinical testing procedure, e.g., to determine the efficacy of a given treatment regimen. Detection can be facilitated by coupling (i.e., physically linking) the antibody to a detectable substance (i.e., antibody labeling). Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}I$, $^{131}I$, $^{35}S$ or $^{3}H$.

Recombinant Expression Vectors, Host Cells and Genetically Engineered Cells

Also included herein are vectors, e.g., expression vectors, containing a nucleic acid encoding a neostatin polypeptide described herein. As used herein, the term "vector" refers to a nucleic acid molecule capable of transporting another nucleic acid to which it has been linked and can include a plasmid, cosmid or viral vector. The vector can be capable of autonomous replication or it can integrate into a host DNA. Viral vectors include, e.g., replication defective retroviruses, adenoviruses and adeno-associated viruses.

A vector can include a neostatin nucleic acid in a form suitable for expression of the nucleic acid in a host cell. Preferably the recombinant expression vector includes one or more regulatory sequences operatively linked to the nucleic acid sequence to be expressed. The term "regulatory sequence" includes promoters, enhancers and other expression control elements (e.g., polyadenylation signals). Regulatory sequences include those which direct constitutive expression of a nucleotide sequence, as well as tissue-specific regulatory and/or inducible sequences. The design of the expression vector can depend on such factors as the choice of the host cell to be transformed, the level of expression of protein desired, and the like. The expression vectors of the invention can be introduced into host cells to thereby produce proteins or polypeptides, including fusion proteins or polypeptides, encoded by nucleic acids as described herein (e.g., neostatin proteins, mutant forms of neostatin proteins, fusion proteins, and the like).

The recombinant expression vectors of the invention can be designed for expression of neostatin proteins in prokaryotic or eukaryotic cells. For example, polypeptides of the invention can be expressed in *E. coli*, insect cells (e.g., using baculovirus expression vectors), yeast cells or mammalian cells. Suitable host cells are discussed further in Goeddel, *Gene Expression Technology: Methods in Enzymology,* 185, (Academic Press, San Diego, Calif. 1990). Alternatively, the recombinant expression vector can be transcribed and translated in vitro, for example using T7 promoter regulatory sequences and T7 polymerase.

Expression of proteins in prokaryotes is most often carried out in *E. coli* with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith, D. B. and Johnson, K. S. (1988) *Gene* 67:31-40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein.

Purified fusion proteins can be used in neostatin activity assays, (e.g., direct assays or competitive assays described in detail below), or to generate antibodies specific for neostatin proteins. In a preferred embodiment, a fusion protein expressed in a retroviral expression vector of the present invention can be used to infect bone marrow cells which are subsequently transplanted into irradiated recipients. The pathology of the subject recipient is then examined after sufficient time has passed (e.g., six weeks).

To maximize recombinant protein expression in *E. coli* is to express the protein in a host bacteria with an impaired capacity to proteolytically cleave the recombinant protein (Gottesman, S., (1990) *Gene Expression Technology: Methods in Enzymology* 185, Academic Press, San Diego, Calif. 119-128). Another strategy is to alter the nucleic acid sequence of the nucleic acid to be inserted into an expression vector so that the individual codons for each amino acid are those preferentially utilized in *E. coli* (Wada et al., (1992) Nucleic Acids Res. 20:2111-2118). Such alteration of nucleic acid sequences of the invention can be carried out by standard DNA synthesis techniques.

The neostatin expression vector can be a yeast expression vector, a vector for expression in insect cells, e.g., a baculovirus expression vector or a vector suitable for expression in mammalian cells.

When used in mammalian cells, the expression vector's control functions are often provided by viral regulatory elements. For example, commonly used promoters are derived from polyoma, Adenovirus 2, cytomegalovirus and Simian Virus 40.

In another embodiment, the recombinant mammalian expression vector is capable of directing expression of the nucleic acid preferentially in a particular cell type (e.g., tissue-specific regulatory elements are used to express the nucleic acid). Non-limiting examples of suitable tissue-specific promoters include the albumin promoter (liver-specific; Pinkert et al. (1987) *Genes Dev.* 1:268-277), lymphoid-specific promoters (Calame and Eaton (1988) *Adv. Immunol.* 43:235-275), in particular promoters of T cell receptors (Winoto and Baltimore (1989) *EMBO J.* 8:729-733) and immunoglobulins (Banerji et al. (1983) Cell 33:729-740; Queen and Baltimore (1983) *Cell* 33:741-748), neuron-specific promoters (e.g., the neurofilament promoter; Byrne and Ruddle (1989) *Proc. Natl. Acad. Sci. USA* 86:5473-5477), pancreas-specific promoters (Edlund et al. (1985) Science 230:912-916), and mammary gland-specific promoters (e.g., milk whey promoter; U.S. Pat. No. 4,873,316 and European Application Publication No. 264, 166). Developmentally-regulated promoters are also encompassed, for example, the murine hox promoters (Kessel and Gruss (1990) *Science* 249:374-379) and the α-fetoprotein promoter (Campes and Tilghman (1989) *Genes Dev.* 3:537-546).

The invention further provides a recombinant expression vector comprising a DNA molecule of the invention cloned into the expression vector in an antisense orientation. Regulatory sequences (e.g., viral promoters and/or enhancers) operatively linked to a nucleic acid cloned in the antisense orientation can be chosen which direct the constitutive, tissue specific or cell type specific expression of antisense RNA in a variety of cell types. The antisense expression vector can be in the form of a recombinant plasmid, phagemid or attenuated virus. For a discussion of the regulation of gene expression using antisense genes see Weintraub, H. et al., (1986) Antisense RNA as a molecular tool for genetic analysis, *Reviews-Trends in Genetics* 1:1.

Another aspect the invention provides a host cell which includes a nucleic acid molecule described herein, e.g., a neostatin nucleic acid molecule within a recombinant expression vector or a neostatin nucleic acid molecule containing sequences which allow it to homologously recombine into a specific site of the host cell's genome. The terms "host cell" and "recombinant host cell" are used interchangeably herein.

Such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, a neostatin protein can be expressed in bacterial cells such as *E. coli*, insect cells, yeast or mammalian cells (such as Chinese hamster ovary cells (CHO) or COS cells). Other suitable host cells are known to those skilled in the art.

Vector DNA can be introduced into host cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation.

A host cell of the invention can be used to produce (i.e., express) a neostatin protein. Accordingly, the invention further provides methods for producing a neostatin protein using the host cells of the invention. In one embodiment, the method includes culturing the host cell of the invention (into which a recombinant expression vector encoding a neostatin protein has been introduced) in a suitable medium such that a neostatin protein is produced. In another embodiment, the method further includes isolating a neostatin protein from the medium or the host cell.

In another aspect, the invention features, a cell or purified preparation of cells which include a neostatin transgene, or which otherwise misexpress neostatin. The cell preparation can consist of human or non human cells, e.g., rodent cells, e.g., mouse or rat cells, rabbit cells, or pig cells. In preferred embodiments, the cell or cells include a neostatin transgene, e.g., a heterologous form of a neostatin, e.g., a gene derived from humans (in the case of a non-human cell). The neostatin transgene can be misexpressed, e.g., overexpressed or underexpressed. In other preferred embodiments, the cell or cells include a gene which misexpress an endogenous neostatin, e.g., a gene the expression of which is disrupted, e.g., a knockout. Such cells can serve as a model for studying disorders which are related to mutated or misexpressed neostatin alleles or for use in drug screening.

In another aspect, the invention features, a human cell, e.g., a hematopoietic stem cell, transformed with nucleic acid which encodes a neostatin polypeptide described herein.

Pharmaceutical Compositions and Methods of Administration

The neostatin and MMP-7 and -14 molecules described herein can be incorporated into pharmaceutical compositions as active ingredients. Such compositions typically include the neostatin or MMP molecule (e.g., a neostatin, MMP-7 or -14 polypeptide, or a nucleic acid molecule comprising a nucleic acid sequence encoding a neostatin, MMP-7 or -14 polypeptide) and a pharmaceutically acceptable carrier. As used herein the language "pharmaceutically acceptable carrier" includes saline, solvents, dispersion media, coatings, antibacterial and antifungal agents, isotonic and absorption delaying agents, and the like, compatible with pharmaceutical administration. Supplementary active compounds can also be incorporated into the compositions.

A pharmaceutical composition is typically formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

In some embodiments, the composition is especially adapted for administration into or around the eye. For example, a composition can be adapted to be used as eye drops, or injected into the eye, e.g., using peribulbar or intravitreal injection. Such compositions should be sterile and substantially endotoxin-free, and within an acceptable range of pH. Certain preservatives are thought not to be good for the eye, so that in some embodiments a non-preserved formulation is used. Formulation of eye medications is known in the art, see, e.g., *Ocular Therapeutics and Drug Delivery: A Multi-Disciplinary Approach*, Reddy, Ed. (CRC Press 1995); Kaur and Kanwar, Drug Dev hid Pharm. 2002 May; 28(5): 473-93; *Clinical Ocular Pharmacology*, Bartlett et al. (Butterworth-Heinemann; 4th edition (Mar. 15, 2001)); and *Ophthalmic Drug Delivery Systems* (*Drugs and the Pharmaceutical Sciences: a Series of Textbooks and Monographs*), Mitra (Marcel Dekker; 2nd Rev&Ex edition (Mar. 1, 2003)).

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It should be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle, which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier for use as a mouthwash. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer. Such methods include those described in U.S. Pat. No. 6,468,798.

Systemic administration of a neostatin, MMP-7 or -14 molecule can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The neostatin, MMP-7 or -14 compounds can also be prepared in the form of suppositories (e.g., with conventional suppository bases such as cocoa butter and other glycerides) or retention enemas for rectal delivery.

Compositions comprising neostatin, MMP-7 or -14 nucleic acid compounds can also be administered by any method suitable for administration of nucleic acid agents. These methods include gene guns, bio injectors, and skin patches as well as needle-free methods such as the microparticle DNA vaccine technology disclosed in U.S. Pat. No. 6,194,389, and the mammalian transdermal needle-free vaccination with powder-form vaccine as disclosed in U.S. Pat. No. 6,168,587. Additionally, intranasal delivery is possible, as described in, inter alia, Hamajima et al. (1998), Clin. Immunol. Immunopathol., 88(2), 205-10. Liposomes (e.g., as described in U.S. Pat. No. 6,472,375) and microencapsulation can also be used. Biodegradable targetable microparticle delivery systems can also be used (e.g., as described in U.S. Pat. No. 6,471,996). In some embodiments, the neostatin, MMP-7 or -14 nucleic acid compounds comprise naked neostatin-, MMP-7- or -14-encoding DNA, and are administered directly, e.g., as described herein.

In some embodiments, the neostatin, MMP-7 or -14 compositions are prepared with carriers that will protect the neostatin, MMP-7 or -14 against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Such formulations can be prepared using standard techniques. The materials can also be obtained commercially, e.g., from Alza Corporation or Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

Dosage, toxicity and therapeutic efficacy of neostatin compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit high therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the 1050 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

An “effective amount” is an amount sufficient to effect beneficial or desired results. For example, a therapeutic amount is one that achieves the desired therapeutic effect. This amount can be the same or different from a prophylactically effective amount, which is an amount necessary to prevent onset of disease or disease symptoms. An effective amount can be administered in one or more administrations, applications or dosages. A therapeutically effective amount of a neostatin, MMP-7 or -14 composition depends on the composition selected. The compositions can be administered one from one or more times per day to one or more times per week; including once every other day. The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of the neostatin compositions of the invention can include a single treatment or a series of treatments.

The pharmaceutical compositions can be included in a container, pack, or dispenser together with instructions for administration.

Methods of Treatment

The neostatin, MMP-7 or -14 polypeptides and nucleic acids described herein are useful in the treatment of opthalmological disorders associated with abnormal angiogenic processes, e.g., a disorder in the formation of blood vessels. Typically, the disorder will stem from overformation of blood vessels, or formation of blood vessels in an unwanted area, e.g., in the avascular regions of the eye, e.g., retinopathies, or in a tumor, e.g., a cancerous or benign tumor. For example, the opthalmological disorder can be age-related macular degeneration, where new blood vessels grow under the retina, or diabetic retinopathy, where abnormal vessels grow on top of the retina. Other opthalmological disorders include retinopathy of prematurity, corneal graft rejection, glaucoma, herpetic and infectious keratitis, ocular ischemia, neovascular glaucoma, corneal, uveal and iris neovascularization, orbital and eyelid tumors, Stevens Johnson Syndrome, ocular cicatricial pemphigoid, wounds, and ocular surface diseases.

The opthalmological disorder may stem from the formation of blood vessels that deliver blood to a tissue, e.g., a primary or metastatic cancerous or benign tumors, e.g., cancer. A metastatic tumor can arise from a multitude of primary tumor types, including but not limited to those of prostate, colon, lung, breast and liver origin.

As used herein, the terms "cancer," "hyperproliferative," and "neoplastic" refer to cells having the capacity for autonomous growth, i.e., an abnormal state or condition characterized by rapidly proliferating cell growth. Hyperproliferative and neoplastic disease states may be categorized as pathologic, i.e., characterizing or constituting a disease state, or may be categorized as non-pathologic, i.e., a deviation from normal but not associated with a disease state. The term is meant to include all types of cancerous growths or oncogenic processes, metastatic tissues or malignantly transformed cells, tissues, or organs, irrespective of histopathologic type or stage of invasiveness. "Pathologic hyperproliferative" cells occur in disease states characterized by malignant tumor growth. Examples of non-pathologic hyperproliferative cells include proliferation of cells associated with wound repair; thus, the methods include administration of a neostatin to maintain avascularity during wound healing. In this embodiment, the opthalmological disorder is a wound, including both accidental as well as intentional wounds (e.g., surgical wounds).

In some embodiments, the opthalmological disorder is a cancer of the eye, e.g., eyelid tumors, e.g., malignant eye lid tumors, benign eye lid tumors, basal cell carcinoma, squamous cell carcinoma, sebaceous cell carcinoma, and malignant melanoma; conjunctival tumors, e.g., pigmented conjunctival tumors, melanoma and primary acquired melanosis with atypia, squamous conjunctival neoplasia, conjunctival lymphoma, and Kaposi's Sarcoma; iris tumors, e.g., iris melanoma, iris pigment epithelial cyst, anterior uveal metastasis, and pearl cyst of the iris; infiltrative intraocular tumors, e.g., multiple myeloma, lymphoma, and leukemia; choroidal tumors, e.g., choroidal melanoma, choroidal metastasis, choroidal nevus, choroidal hemangioma, choroidal osteoma, and Nevus of Ota; retinal tumors, e.g., retinoblastoma, retinal pigment epithelial tumors, retinal pigment epithelial hypertrophy, von Hippel angioma; optic nerve tumors, e.g., melanocytoma, melanoma, meningioma, circumpapillary metastasis; orbital tumors, e.g., lymphangioma, cavernous hemangioma, meningioma, mucocele, rhabdomyosarcoma, orbital pseudotumor, adenoid cystic carcinoma, periocular hemangioma of childhood; cancers of the ocular adnexa, e.g., lacrimal gland carcinomas such as adenoid cystic carcinoma and mucoepidermal epithelioma; and metastatic ocular tumors, e.g., metastatic choroidal melanoma, and metastatic retinoblastoma.

As used in this context, to "treat" means to ameliorate at least one symptom associated with abnormal angiogenesis as well as reduce neovascularization. For the treatment of cancers and solid tumors, to "treat" includes inhibition of the growth of blood vessels resulting in a lack of nutrients for the tumors and/or cancer cells needed by the tumor for its growth. Tumors and growths will decrease in size and possibly disappear. Administration of a therapeutically effective amount of a neostatin, MMP-7, or -14 composition for the treatment of arthritic conditions will result in decreased blood vessel formation in cartilage, specifically joints, resulting in increased mobility and flexibility in these regions. In opthalmologic conditions, e.g., diabetic retinopathy, administration of a therapeutically effective amount of a neostatin, MMP-7, or -14 composition will reduce the formation of extraneous blood vessels in the retina, resulting in unobstructed vision. In the treatment of disorders such as Kaposi's Sarcoma, administration of a therapeutically effective amount of a neostatin, MMP-7, or -14 composition will inhibit the growth and/or further formation of blood vessels, thereby inhibiting the formation of any lesions and/or tumors that arise.

Methods of Screening

The invention includes methods for screening test compounds, e.g., small molecule test compounds, e.g., compounds that are initially members of an organic chemical library, to identify agents useful in the treatment of opthalmological disorders associated with abnormal angiogenic processes, e.g., agents that increase the activity of MMP-7 and/or MMP-14, or otherwise cause an increase in levels of neostatin-7 or -14.

As used herein, "small molecules" refers to small organic or inorganic molecules of molecular weight below about 3,000 Daltons. In general, small molecules useful for the invention have a molecular weight of less than 3,000 Daltons (Da). The small molecules can be, e.g., from at least about 100 Da to about 3,000 Da (e.g., between about 100 to about 3,000 Da, about 100 to about 2500 Da, about 100 to about 2,000 Da, about 100 to about 1,750 Da, about 100 to about 1,500 Da, about 100 to about 1,250 Da, about 100 to about 1,000 Da, about 100 to about 750 Da, about 100 to about 500 Da, about 200 to about 1500, about 500 to about 1000, about 300 to about 1000 Da, or about 100 to about 250 Da).

The small molecules can be natural products or members of a combinatorial chemistry library. A set of diverse molecules should be used to cover a variety of functions such as charge, aromaticity, hydrogen bonding, flexibility, size, length of side chain, hydrophobicity, and rigidity. Combinatorial techniques suitable for synthesizing small molecules are known in the art, e.g., as exemplified by Obrecht and Villalgordo, *Solid-Supported Combinatorial and Parallel Synthesis of Small-Molecular-Weight Compound Libraries*, Pergamon-Elsevier Science Limited (1998), and include those such as the "split and pool" or "parallel" synthesis techniques, solid-phase and solution-phase techniques, and encoding techniques (see, for example, Czarnik, Cum Opin. Chem. Bio. 1:60-6 (1997)). In addition, a number of small molecule libraries are commercially available. A number of suitable small molecule test compounds are listed in U.S. Pat. No. 6,503,713, incorporated herein by reference in its entirety Libraries screened using the methods of the present invention can comprise a variety of types of small molecule test compounds. A given library can comprise a set of structurally related or unrelated small molecule test compounds. In some embodiments, the test compounds are peptide or peptidomimetic molecules. In some embodiments, the small molecules are nucleic acids.

In some embodiments, the small organic molecules and libraries thereof can be obtained by systematically altering the structure of a first small molecule, e.g., a first small molecule that is structurally similar to a known natural binding partner of the target polypeptide, or a first small molecule identified as capable of binding the target polypeptide, e.g., using methods known in the art or the methods described herein, and correlating that structure to a resulting biological activity, e.g., a structure-activity relationship study. As one of skill in the art will appreciate, there are a variety of standard methods for creating such a structure-activity relationship. Thus, in some instances, the work may be largely empirical, and in others, the three-dimensional structure of an endogenous polypeptide or portion thereof can be used as a starting point for the rational design of a small molecule compound or compounds. For example, in one embodiment, a general library of small molecules is screened, e.g., using the methods described herein.

Small molecules identified as "hits" (e.g., small molecules that demonstrate an increase in MMP-7, MMP-14, neostatin-7, or neostatin-14 levels or activity) in the first screen can be selected and systematically altered, e.g., using rational design, to optimize binding affinity, avidity, specificity, or other parameter. Such optimization can also be screened for using the methods described herein. Thus, in one embodiment, the invention includes screening a first library of small molecules using a method known in the art and/or described herein, identifying one or more hits in that library, subjecting those hits to systematic structural alteration to create a second libraries of compounds structurally related to the hit, and screening the second library using the methods described herein.

Small molecules identified as hits can be considered candidate therapeutic compounds, useful in treating opthalmological disorders associated with neovascularization, as described herein. A variety of techniques useful for determining the structures of "hits" can be used in the methods described herein, e.g., NMR, mass spectrometry, gas chromatography equipped with Electron capture detectors, fluorescence and absorption spectroscopy. Thus, the invention also includes compounds identified as "hits" by the methods described herein, and methods for their administration and use in the treatment, prevention, or delay of development or progression of a disorder described herein.

Small molecules identified candidate therapeutic compounds can be further screened by administration to an animal model of an opthalmological disorders associated with neovascularization, as described herein. The animal can be monitored for a change in the disorder, e.g., for an improvement in a parameter of the disorder. In some embodiments, the parameter is unwanted vascularisation, and an improvement would be a decrease in the levels of vascularisation.

The invention is further described in the following examples, which do not limit the scope of the invention described in the claims.

EXAMPLES

Anti-Type XVIII Collagen Antibodies

Antibodies used in this project included antibodies generated against the NC 1 domain (hinge region anti-neostatin) and endostatin domain (anti-endostatin) as described by Lin et al ((2001), Invest. Opthalmol. Vis. Sci. 42:2517-24), as well as commercially available antibodies.

Generation of Recombinant His-Endostatin, His-Neostatin-7 and His-Neostatin-14.

Mouse collagen XVIII cDNAs containing endostatin and neostatin were amplified using polymerase chain reaction (PCR) from the NC1 fragment and subcloned into the pET28A vector (Sasaki et al., (2000), J. Mol. Biol. 301:1179-90). The primers used were as follows: 5' XVIII neostatin-7 CCTGAGGCACGGAATTCCAGGTGGCTGCTTTCC (SEQ ID NO:10); 5'XVIII neostatin-14 GTTCCACATCACCACGAATTCTATGTGCACCTGCCGCCAGCCCGC (SEQ ID NO:11); 5 XVIII endo: CACCACAGTTCCTATGAATTCCTGCCGCCAGCCCGC (SEQ ID NO:12); and 3' XVIII endo CTGCCACCCTAGCTGGCGGCCGCCTATTTGGAGAAAGAGG (SEQ ID NO:13). These constructs were transformed into *E. coli* (BL21DE3) and a single colony was isolated for each construct. The bacteria were grown to semi-log phase, then induced with 0.3 hmM of IPTG to produce His-endostatin and His-neostatin. Bacteria were lysed with 8M urea in PBS and the protein was isolated using a Ni-bead column. His-endostatin and His-neostatin were eluted with 40 mM imidazole and dialyzed against PBS. The purity of the His-fusion proteins was determined by Coomassie Brilliant blue staining and Western blot analysis. In addition, cDNA fragments of type XVIII collagen (endostatin and neostatin) were subcloned into eukaryotic expression vectors (pEF) with an Igk leader peptide. Although this approach produced reasonable levels of protein, both the His-endostatin and His-neostatins showed unacceptably high levels of aggregation that reduced the yield and may affect the characteristics and functions of these molecules.

MMP Cleavage Assays and Purification of Neostatins-7 and -14

One hundred nanograms of C-flag-tagged Type XVIII collagen NC1 fragments were cleaved with various activated MMPs (MMP-2, -7 and -9 activated by 4-aminophenylmercuric acetate (APMA) and MMP-14. Proteolytic fragments were analyzed by Western blot analysis with anti-endostatin or anti-C-flag (M2) antibody (Sigma, Mo.). MMP-7 cleavage of NC1 fragments were performed at various pH (pH=5.5, 6.5 and 7.5) conditions to determine ideal method of generating enough quantities of MMP-derived neostatins to be used for CPAE assays and in vivo therapeutic testing.

The yield of neostatins using this approach was lower than the recombinant approach; the quantities of MMP-derived neostatins were sufficient to proceed with western blot analyses, but not with the functional assays.

CPAE Proliferation Assay

Bovine CPAE cells were grown to confluence in Dulbecco's Modified Eagle Medium (DMEM) with 10% fetal calf serum (FCS) and kept confluent for 48 hours. The cells were harvested by trypsinization at 37° C. for 5 minutes. A suspension of 2,000 cells in DMEM with 0.5% FCS was added to each well of a 96-well plate coated with 10 μg/ml fibronectin and incubated for 24 hours at 37° C. The medium was removed and replaced with DMEM-containing 0.5% FCS (unstimulated cells) or 10% FCS (stimulated and treated cells) in the presence or absence of recombinant endostatin and neostatin. After the 48 hour proliferation period, cell density was determined using a Formazin turbidity detection kit. Controls were cultured in similar fashion.

Corneal Pocket Assay with bFGF in the Presence of Naked DNA (Murine pEF-Neostatin-7, pEF-14, and Vector Control)

A 0.5 mm incision perpendicular to the mouse corneal surface traversing the epithelium and anterior stroma was performed with a ½-inch 30-gauge needle (Becton Dickinson, Franklin Lakes, N.J.). A ½-inch 33-gauge needle attached to a 10 μl gas tight syringe (Hamilton, Reno, Nev.) was introduced into the corneal stroma and advanced towards an area half the distance between an imaginary line drawn from the limbus to the corneal center. Turning the bevel towards the center of the cornea, plasmid (2 ul of pEF, pEF-endostatin, pEF-neostatin 7 or pEF-neostatin 14) solution was forcibly injected into the stroma.

A corneal micropocket assay, as previously described by Kato et al., was carried out three days after corneal naked DNA injection. Briefly, wild type mice (C57BL/6) were anesthetized by an intraperitoneal injection of ketamine and xylazine. Proparacaine HCl eye drops were used for local anesthesia. Corneal micropockets were created with a modified von Graefe knife. Uniformly sized hydron pellets containing 80 ng of human bFGF (R&D Systems, Minneapolis, Minn., USA) and 40 ug of sucrose aluminum sulfate were implanted into corneal pockets at day 4 after naked DNA injection. Ofloxacin eye drops were instilled after surgery. The eyes were examined and photographed on day 0, 1, 4, 7, 10 and 14 post pellet implantation by slit lamp microscopy (Nikon, Tokyo, Japan). Color images were magnified 100× to allow precise measurement of corneal neovascularization. The neovascular area was calculated using a modified NIH imaging program to correct for parallax.

Example 1

Cleavage of the NC1 Region with Matrix Metalloproteinases (MMP)-2, -7, -9 and -14

To determined whether collagen XVIII could be cleaved by different matrix metalloproteinases, recombinant NC1 fragments of collagen XVIII were generated in cultured 293T cells as described by Sasaki et al. (FIG. 1A). The recombinant NC1 fragments were isolated in serum-free medium with Heparin Sepharose™. Fragments were incubated with MMP-2, -7, -9 and -14 (FIG. 1A) at a concentration of 0.01 ug protein/0.1 mg active enzyme. Treatment of the recombinant NC1 fragment of type XVIII collagen with MMP-2 or -9, similar to control, did not produce NC1 degradation products. However, MMP-7 and MMP-14 cleaved the recombinant NC1 fragment to produce neostatin-7, neostatin-14 and several endostatin-containing fragments.

Fragments produced by MMP-14 cleavage of NC1 were subjected to Edman degradation protein sequencing. One of the sequenced fragments has a N-terminal sequence of xVHLRPARPG (SEQ ID NO:14). Thus, the MMP-14 cleavage site of NC1 fragment of type XVIII collagen residue is located between MMP-7 cleavage site and cathepsin L cleavage site. The MMP-14 cleavage site of NC1 fragments is in agreement with the protease-sensitive site of naturally occurring type XVIII collagen in the blood.

These results demonstrate that the NC1 region of Collagen XVIII is cleaved by metalloproteinases other than elastase and cathepsin L.

Example 2

Figure 2A:
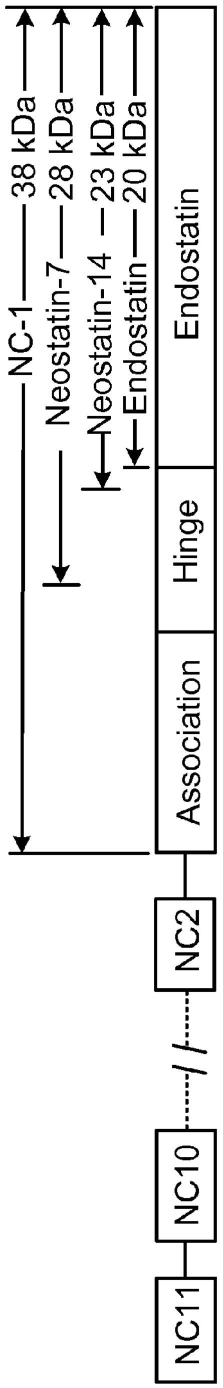
FIG. 2A is a schematic illustration of Type XVIII collagen shown the relationship of the NC1 region, neostatin-7 and -14, and endostatin.
Figure 2B:
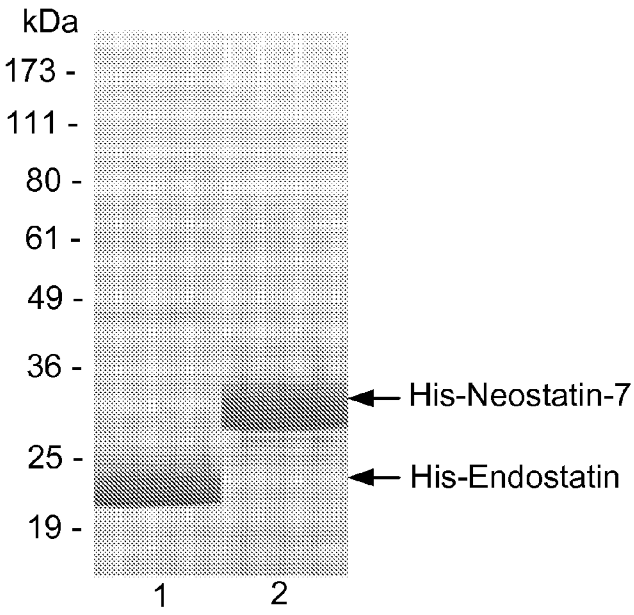
FIG. 2B is a reproduction of an SDS-PAGE gel showing recombinant endostatin and neostatin-7 isolated using Ni beads and eluted by 40 mM imidazole; the gel was stained with Coomassie™ Brilliant Blue.

The Effects of His-endostatin and His-neostatin on Endothelial Cell Proliferation To determine the effect of MMP-7 degradation fragments of collagen XVIII/NC1, recombinant histidine-tagged endostatin (His-endostatin) and histidine-tagged neostatin-7 (His-neostatin-7) were generated from bacterial lysate and purified using Ni-beads. His-endostatin and His-neostatin-7 were eluted with 40 mM imidazole, and analyzed with SDS-PAGE (SDS-polyacrylamide gel electrophoresis) and resulted in the production of bands corresponding to the molecular weight of His-endostatin (~20 kDa) and His-neostatin-7 (~28 kDa) by Coomassie brilliant blue staining (FIG. 2B). His-endostatin and His-neostatin-7 were characterized by Western blot analysis with anti-endostatin antibodies. His-fusion proteins showed molecular weight bands of 20 kDa (FIG. 2C lane 1) and 28 kDa (FIG. 2C lane 2) representing His-endostatin and His-neostatin-7, respectively.

Figure 2D:
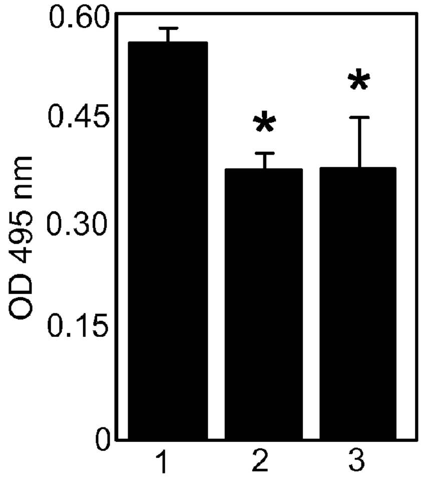
FIG. 2D is a bar graph illustrating the effects of recombinant endostatin (bar 2, 10% FCS+2.5 ug/ml endostatin) and neostatin-7 (bar 3, 10% FCS+2.5 ug/ml neostatin) on CPAE cell proliferation as compared to untreated control CPAE cells (bar 1, 10% FCS).
Figure 2C:
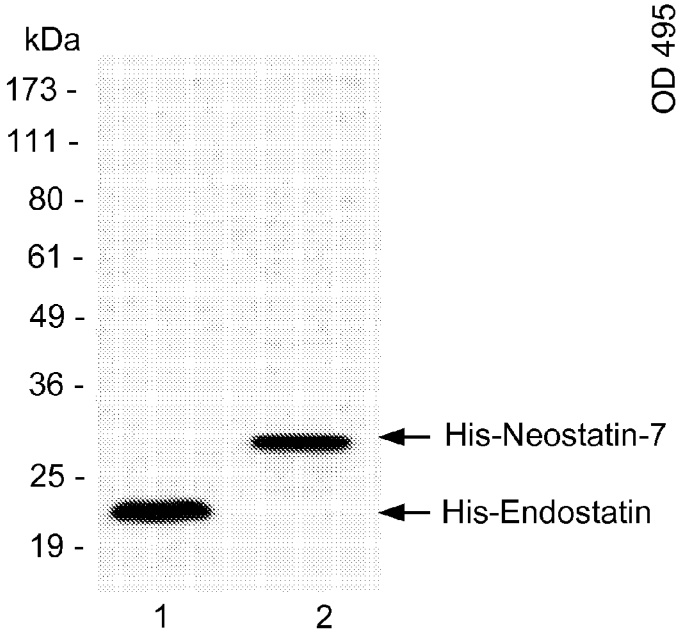
FIG. 2C is a Western blot showing recombinant endostatin (lane 1) and neostatin (lane 2), visualized using anti-endostatin antibodies.

To compare the effect of recombinant endostatin and neostatin-7 on vascular endothelial cell proliferation in vitro, we added 2.5 mg/ml of endostatin with 10% FCS and 2.5 mg/ml neostatin-7 with 10% FCS to the cultured CPAE cells (FIG. 2D). As shown in FIG. 2D, recombinant neostatin and recombinant endostatin inhibited CPAE proliferation, $OD_{495}$=0.378±0.04 (bar 3) and $OD_{495}$=0.375±0.015 (bar 2), respectively, when compared to untreated control cells (10% FCS) $OD_{495}$=0.46±0.02. (bar 1). These results indicate that recombinant histidine-tagged neostatin-7 can inhibit proliferation of arterial endothelial cells.

Example 3 pH Affects MMP-7 Cleavage of NC1 Fragments of Type XVIII Collagen

Figure 3B:
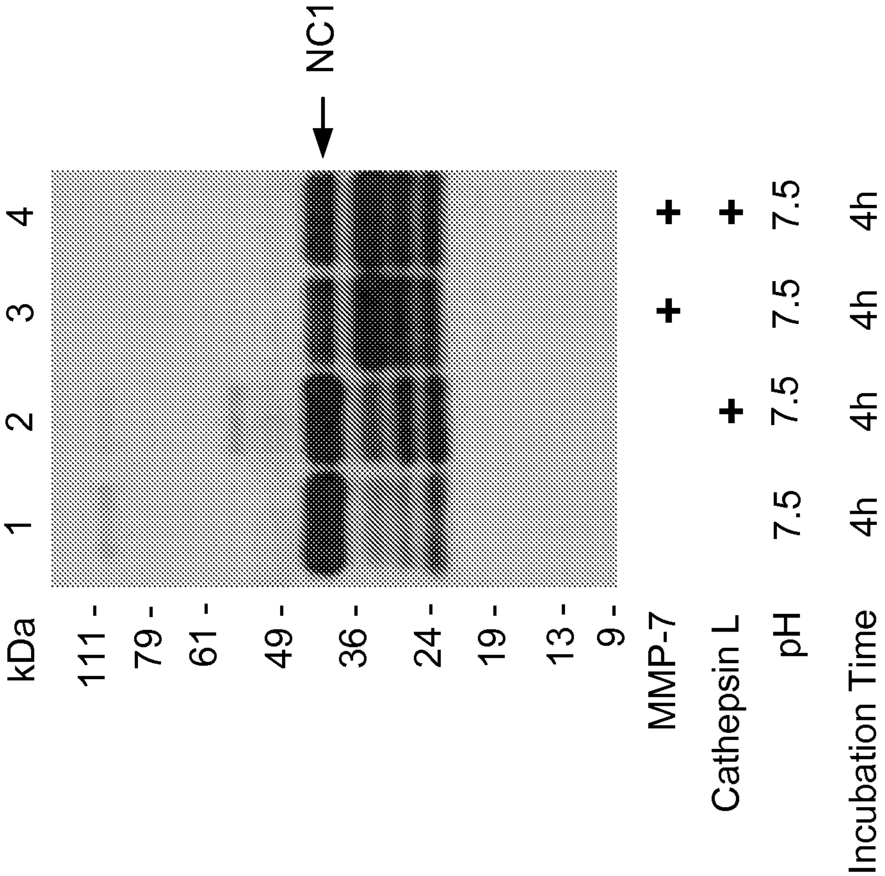
FIG. 3B is a reproduction of a gel showing that cathepsin L did not interfere with the cleavage of NC1 fragments by MMP-7. Recombinant NC1 was incubated with MMP-7 (lane 2) or cathepsin L and MMP-7 (lane 3) at pH 7.5 for 4 hrs (lane 1=control).
Figure 3A:
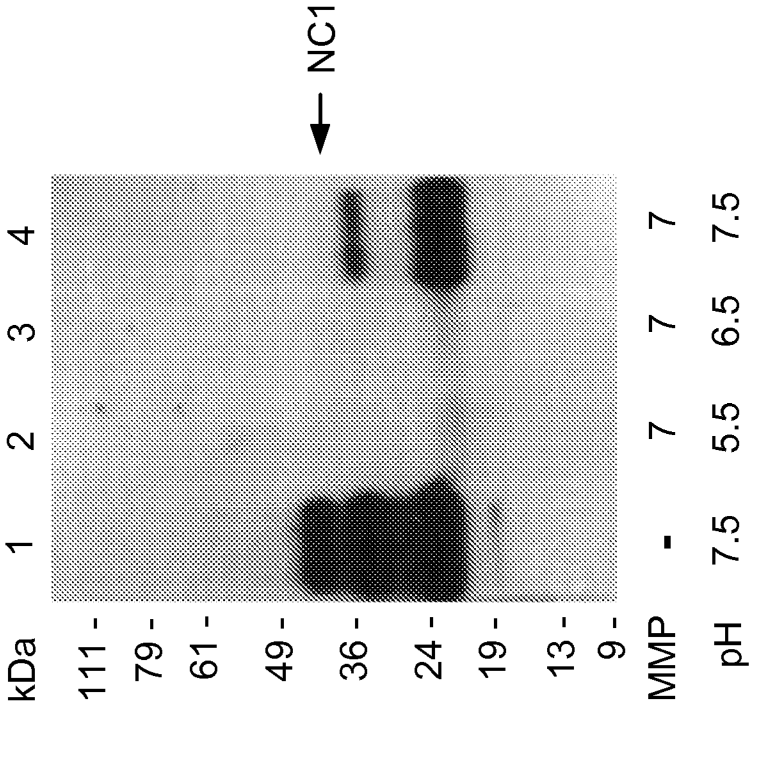
FIG. 3A is a reproduction of a gel showing the influence of pH on MMP-7 cleavage of recombinant NC1 (lane 1, control, pH 7.5; lane 2, pH=5.5; lane 3, pH=6.5; lane 4, pH=7.5).

To determine whether the cleavage of collagen XVIII/NC1 by MMP-7 is pH sensitive, NC1 fragments were incubated with MMP-7 at various pH (FIG. 3A; pH=5.5, 6.5 and 7.5. In addition, recombinant NC1 fragments were incubated with MMP-7 (lane 2), and a combination of cathepsin L and MMP-7 (lane 3); compared to control (lane 1). NC1 fragments were processed to generate several endostatin-containing fragments. In FIG. 3B, accumulation of 28 kDa fragments and diminished NC1 fragments were found in lanes 2 and 3, but not in lane 1. Cathepsin L did not interfere with the cleavage of NC1 fragments by MMP-7. These results indicate that the cleavage of collagen XVIII/NC1 by MMP-7 is pH sensitive, and proceeds less efficiently at more acidic pH.

Example 4

Naked pEF-Neostatin DNA Blocked bFGF-Induced Corneal Neovascularization

To determine whether neostatin-7 can inhibit bFGF induced corneal neovascularization, mouse corneas were injected with naked pEF-Igk and pEF-neostatin-7.

Figure 4:
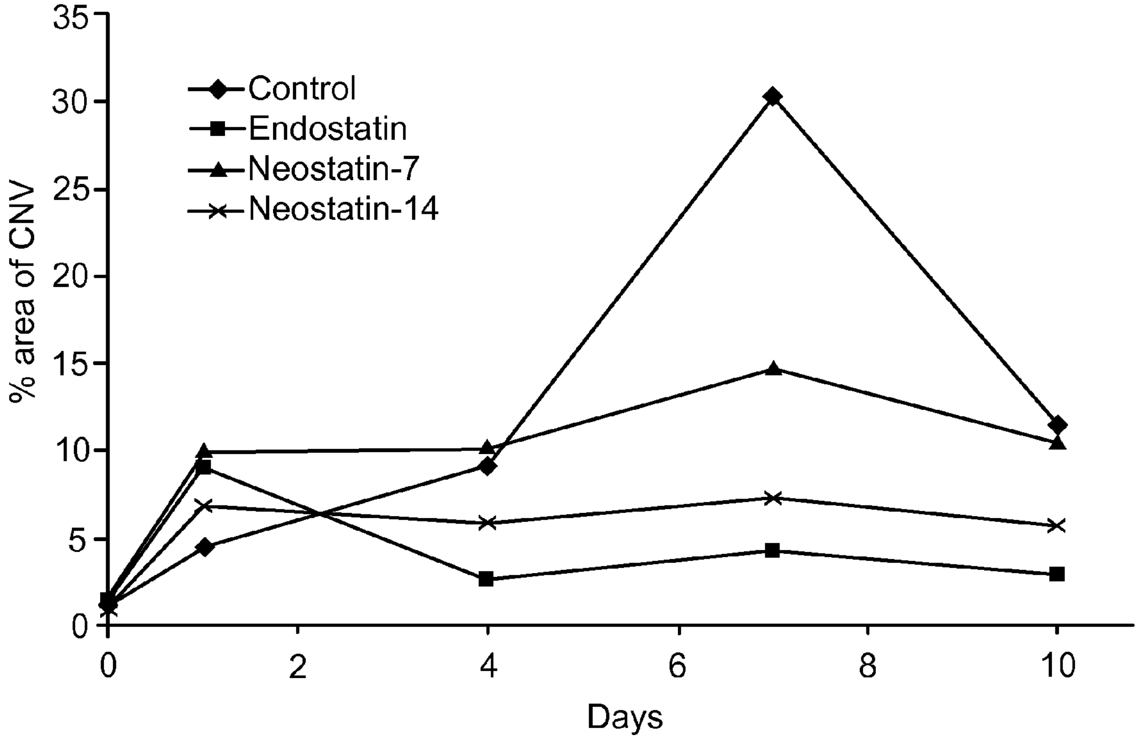
FIG. 4 is a line graph illustrating areas of corneal neovascularization at various time points analyzed in mouse eyes injected with naked DNA (pEF control, pEF-endostatin, pEF-neostatin-7 or pEF-neostatin-14) three days before bFGF pellet implantation. Corneal neovascularization was observed at day 1, 4, 7, 10 and 14. The measured areas of corneal neovascularization at various time points were analyzed in the endostatin, neostatins and vector control groups using a modified NIH image program as described in Kure et al.

Naked DNA has been effectively used for the delivery of DNA into mouse corneas (Stechschulte et al., (2001) Invest. Opthalmol. Vis. Sci. 42:1975-9). To determine whether neostatin-7 and neostatin-14 can inhibit bFGF induced corneal neovascularization, mouse corneas were injected with naked DNA of pEF, pEF-endostatin, pEF-neostatin-7 and pEF-neostatin-14. A bFGF pellet (80 ng) was implanted into mouse corneas 72 hours post DNA injection (pEF, pEF-endostatin, pEF-neostatin-7, pEF-neostatin-14). The areas of corneal neovascularization were calculated using a modified NIH imaging program (e.g., as described in Kure et al., (2001) FEBS Lett. 508:187-90) and graphed (FIG. 4). Areas of corneal neovascularization measured at day 1, 4, 7, 10 and 14 were as shown in Table 1.

TABLE 1

| Corneal Vascularisation | | | | | |
|---|---|---|---|---|---|
| | Day | | | | |
| DNA | 1 | 4 | 7 | 10 | 14 |
| control pEF (empty) | 1.111 $mm^2$ ± 0.003 $mm^2$ | 4.49 $mm^2$ ± 0.01 $mm^2$ | 9.24 $mm^2$ ± 0.01 $mm^2$ | 30.34 $mm^2$ ± 0.08 $mm^2$ | 11.479 $mm^2$ ± 0.06 $mm^2$ |
| pEF-endostatin | 1.456 $mm^2$ ± 0.001 $mm^2$ | 9.09 $mm^2$ ± 0.03 $mm^2$ | 2.603 $mm^2$ ± 0.001 $mm^2$ | 4.261 $mm^2$ ± 0.008 $mm^2$ | $2.89^2$ $mm^2$ ± 0.001 $mm^2$ |
| pEF-neostatin-7 | 1.640 mm2 ± 0.002 $mm^2$ | 9.955 $mm^2$ ± 0.025 $mm^2$ | 10.108 $mm^2$ ± 0.011 $mm^2$ | 14.661 $mm^2$ ± 0.08 $mm^2$ | 10.429 $mm^2$ ± 0.018 $mm^2$ |
| pEF-neostatin-14 | 0.956 $mm^2$ ± 0.04 $mm^2$ | 6.875 $mm^2$ ± 0.016 $mm^2$ | 5.834 $mm^2$ ± 0.006 $mm^2$ | 7.341 $mm^2$ ± 0.006 $mm^2$ | 5.698 $mm^2$ ± 0.02 $mm^2$ |

Diminished corneal neovascularization was observed after pEF-endostatin, pEF-neostatin-7 and pEF-neostatin-14 DNA injection at day 4, 7 and 10 as compared to controls. As a control, mouse corneas were injected with naked DNA (pEF, pEF-endostatin, pEF-neostatin-7) without bFGF pellet implantation; no corneal neovascularization was observed at days 4, 7 and 10.

These results indicate that neostatin-7 and -14, delivered as naked DNA, can inhibit bFGF induced corneal neovascularization.

REFERENCES

[1] Halfter W, Dong S, Schurer B, Cole G J. (1998) J Biol. Chem. 273, 25404-12.

[2] Kreuger J, Matsumoto T, Vanwildemeersch M, Sasaki T, Timpl R, Claesson-Welsh L, Spillmann D, Lindahl U. (2002) EMBO J. 21, 6303-11.

[3] Lin H C, Chang J H, Jain S, Gabison E E, Kure T, Kato T, Fukai N, Azar D T (2001) Invest Opthalmol V is Sci 42, 2517-24.

[4] Kure T, Chang J H, Kato T, Hernandez-Quintela E, Ye H, Lu P C, Matrisian L M, Gatinel D, Shapiro S, Gosheh F, Azar DT. (2001) FEBS Lett 508, 187-90.

[5] O'Reilly M S, Boehm T, Shing Y, Fukai N, Vasios G, Lane W S, Flynn E, Birkhead J R, Olsen B R, Folkman J. (1997) Cell 88, 277-85.

[6] Sasaki T, Fukai N, Mann K, Gohring W, Olsen B R, Timpl R. (1998) EMBO J. 17, 4249-56

[7] Wen W, Moses M A, Wiederschain D, Arbiser J L, Folkman J. (1999) Cancer Res 59, 6052-6.

[8] Felbor U, Dreier L, Bryant R A, Ploegh H L, Olsen B R, Mothes W (2000) EMBO J 19, 1187-94.

[9] Lu P C, Ye H, Maeda M, Azar D T (1999). Invest Opthalmol V is Sci 40, 20-7.

[10] Ye, H. Q. and D. T. Azar (1998). Invest Opthalmol V is Sci 39, 913-21.

[11] Ye H Q, Maeda M, Yu F S, Azar D T. (2000). Invest Opthalmol V is Sci 41, 2894-9.

[12] Fukai N, Eklund L, Marneros A G, Oh S P, Keene D R, Tamarkin L, Niemela M, Ilves M, Li E, Pihlajaniemi T, Olsen B R. (2002). EMBO J. 21, 1535-44.

[13] Sasaki T, Larsson H, Tisi D, Claesson-Welsh L, Hohenester E, Timpl R. (2000). J Mol Biol 301, 1179-90.

[14] Kure T, Chang J H, Kato T, Hernandez-Quintela E, Ye H, Lu P C, Matrisian L M, Gatinel D, Shapiro S, Gosheh F, Azar D T, (2003) Invest Opthalmol V is Sci 44, 137-44.

[15] Stechschulte S U, Joussen A M, von Recum H A, Poulaki V, Moromizato Y, Yuan J, D'Amato R J, Kuo C, Adamis A P. (2001) Invest Opthalmol V is Sci. 42, 1975-9

[16] Ferreras M, Felbor U, Lenhard T, Olsen B R, Delaisse J. (2000) FEBS Lett. 486, 247-51.

[17] Woessner J F Jr, Taplin C J. (1998) J Biol. Chem. 263, 16918-25.

[18] Patterson B C, Sang Q A. (1997) J Biol. Chem. 272, 28823-5.

[19] Chang, J. H., E. E. Gabison, et al. (2001). Curr Opin Opthalmol 12, 242-9.

[20] Colorado P C, Torre A, Kamphaus G, Maeshima Y, Hopfer H, Takahashi K, Volk R, Zamborsky E D, Herman S, Sarkar P K, Ericksen M B, Dhanabal M, Simons M, Post M, Kufe D W, Weichselbaum R R, Sukhatme V P, Kalluri R. (2000). Cancer Res 60, 2520-6.

[21] Marneros, A. G. and B. R. Olsen (2001). Matrix Biol 20, 337-45.

[22] Shichiri, M. and Y. Hirata (2001) FASEB J 15, 1044-53.

[23] Lee S J, Jang J W, Kim Y M, Lee H I, Jeon J Y, Kwon Y G, Lee S T. (2002) FEBS Lett. 519, 147-52.

[24] Rehn M, Veikkola T, Kukk-Valdre E, Nakamura H, Ilmonen M, Lombardo C, Pihlajaniemi T, Alitalo K, Vuori K. (2001). Proc Natl Acad Sci USA 98, 1024-9.

[25] Kim Y M, Jang J W, Lee O H, Yeon J, Choi E Y, Kim K W, Lee S T, Kwon Y G. (2000). Cancer Res 60, 5410-3.

[26] Kim Y M, Hwang S, Kim Y M, Pyun B J, Kim T Y, Lee S T, Gho Y S, Kwon Y G. (2002) J. Biol Chem 277, 27872-9

[27] Javaherian K, Park S Y, Pickl W F, LaMontagne K R, Sjin R T, Gillies S, Lo K M. (2002) J Biol Chem 277, 45211-8

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of inhibiting or delaying progression of corneal neovascularization associated with increased levels of bFGF in a patient, the method comprising administering to the eye of the patient a therapeutically effective amount of a composition comprising an expression vector comprising an isolated nucleic acid molecule encoding the polypeptide of SEQ ID NO:2 or 4, operatively linked to a promoter, wherein expression of said polypeptide results in inhibition or delaying of the progression of bFGF-associated corneal neovascularization.

2. A method of inhibiting or delaying progression of corneal neovascularization associated with increased levels of bFGF in a patient, the method comprising administering to the eye of the patient a therapeutically effective amount of a composition comprising an expression vector comprising a nucleic acid molecule encoding a fusion protein, wherein the fusion protein comprises amino acid sequence of SEQ ID NO:2 or 4 linked to a non-collagen XVIII amino acid sequence, the nucleic acid molecule is operatively linked to a promoter, and expression of said fusion protein results in inhibition or delaying of the progression of bFGF-associated corneal neovascularization.

3. The method of claim 1, wherein the composition further comprises a pharmaceutically acceptable carrier.

4. The method of claim 2, wherein the composition further comprises a pharmaceutically acceptable carrier.

5. The method of claim 1, wherein the nucleic acid molecule encodes the polypeptide of ID NO:2.

6. The method of claim 1, wherein the nucleic acid molecule encodes the polypeptide of ID NO:4.

7. The method of claim 2, wherein the fusion protein comprises the polypeptide of SEQ ID NO:2.

8. The method of claim 2, wherein the fusion protein comprises the polypeptide of SEQ ID NO:4.

9. A method of inhibiting or delaying progression of corneal neovascularization associated with increased levels of bFGF during wound healing in a patient, the method comprising administering to the eye of the patient a therapeutically effective amount of a composition comprising an expression vector comprising an isolated nucleic acid molecule encoding the polypeptide of SEQ ID NO:2 or 4, operatively linked to a promoter, wherein expression of said polypeptide results in inhibition or delaying of the progression of corneal neovascularization of bFGF-associated corneal neovascularization during wound healing.

10. The method of claim 9, wherein the composition further comprises a pharmaceutically acceptable carrier.

11. The method of claim 9, wherein the nucleic acid molecule encodes the polypeptide of SEQ ID NO:2.

12. The method of claim 9, wherein the nucleic acid molecule encodes the polypeptide of SEQ ID NO:4.

13. The method of claim 9, wherein the wound is a surgical wound.

* * * * *

UNITED STATES PATENT AND TRADEMARK OFFICE

CERTIFICATE OF CORRECTION

PATENT NO. : 8,492,141 B2
APPLICATION NO. : 12/766741
DATED : July 23, 2013
INVENTOR(S) : Dimitri T. Azar and Jin-Hong Chang It is certified that error appears in the above-identified patent and that said Letters Patent is hereby corrected as shown below:

On the Title page, column 2 (Abstract), line 3, delete "opthalmological" and insert -- ophthalmological --

In the Claims:

In column 45, line 27, claim 2, delete "amino" and insert -- the amino --

Signed and Sealed this
Fifth Day of November, 2013

Teresa Stanek Rea
*Deputy Director of the United States Patent and Trademark Office*